(12) United States Patent
Djupesland

(10) Patent No.: US 10,124,132 B2
(45) Date of Patent: Nov. 13, 2018

(54) NASAL DELIVERY

(71) Applicant: OptiNose AS, Oslo (NO)

(72) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 0 days.

(21) Appl. No.: 15/051,622

(22) Filed: Feb. 23, 2016

(65) Prior Publication Data
US 2016/0367772 A1 Dec. 22, 2016

Related U.S. Application Data

(60) Division of application No. 14/047,390, filed on Oct. 7, 2013, which is a continuation of application No.
(Continued)

(30) Foreign Application Priority Data

Mar. 6, 2006 (GB) .................................. 0604444.0

(51) Int. Cl.
*A61M 11/00* (2006.01)
*A61M 15/08* (2006.01)
(Continued)

(52) U.S. Cl.
CPC ............ *A61M 15/08* (2013.01); *A61M 11/00* (2013.01); *A61M 15/009* (2013.01);
(Continued)

(58) Field of Classification Search
USPC ............. 128/206.11, 207.18, 203.18–203.22, 128/203.12
See application file for complete search history.

(56) References Cited

U.S. PATENT DOCUMENTS

| 605,436 A | 6/1898 | Kellogg |
| 642,748 A | 2/1900 | Manners |

(Continued)

FOREIGN PATENT DOCUMENTS

| WO | WO 1993/024164 | 12/1993 |
| WO | WO 96/22802 | 8/1996 |

(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Stephen R Crow
(74) *Attorney, Agent, or Firm* — Finnegan, Henderson, Farabow, Garrett & Dunner, LLP

(57) ABSTRACT

A nasal delivery device for and method of delivering substance to a nasal cavity of a subject, the delivery device comprising: a nosepiece unit including a nosepiece for fitting to a nostril of a subject and a nozzle through which substance is in use delivered, preferably substantially axially to a longitudinal axis of the nosepiece, to the respective nasal cavity, wherein at least a tip element of the nosepiece has, at least in one configuration, an elongate lateral section which has a longer dimension in a first, sagittal direction than a second direction orthogonal to the sagittal direction, such that, when the nosepiece is inserted in the nasal cavity of the subject, the longer dimension of the nosepiece acts to engage lower and upper surfaces of the nasal cavity, preferably at the nasal valve, and expand the same in the sagittal plane; and a delivery unit for delivering substance through the nozzle of the nosepiece.

25 Claims, 46 Drawing Sheets

Related U.S. Application Data

12/281,894, filed as application No. PCT/IB2007/001709 on Mar. 6, 2007, now Pat. No. 8,550,073.

(51) Int. Cl.
*A61M 31/00* (2006.01)
*A61M 15/00* (2006.01)

(52) U.S. Cl.
CPC .... *A61M 15/0021* (2014.02); *A61M 15/0098* (2014.02); *A61M 15/085* (2014.02); *A61M 31/00* (2013.01); *A61M 15/0091* (2013.01); *A61M 2202/064* (2013.01)

(56) References Cited

U.S. PATENT DOCUMENTS

| | | | |
|---|---|---|---|
| 746,749 A | 12/1903 | Seidel | |
| 4,227,522 A | 10/1980 | Carris | |
| 4,513,891 A | 4/1985 | Hain et al. | |
| 4,648,398 A | 3/1987 | Agdanowski et al. | |
| 5,797,390 A | 8/1998 | McSoley | |
| 5,797,392 A | 8/1998 | Keldmann et al. | |
| 6,561,193 B1 | 5/2003 | Noble | |
| 6,647,980 B1 | 11/2003 | Gizuararson | |
| 6,648,848 B1 | 11/2003 | Keldmann et al. | |
| 6,715,485 B1 | 4/2004 | Djupesland | |
| D530,815 S | 10/2006 | Murphy et al. | |
| 7,204,246 B1* | 4/2007 | Berinato | A61M 15/08 128/200.14 |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2* | 7/2011 | Djupesland | A61M 15/0091 128/200.13 |
| 8,047,202 B2 | 11/2011 | Djupesland | |
| 8,136,527 B2* | 3/2012 | Wondka | A61M 16/00 128/200.24 |
| 8,146,589 B2 | 4/2012 | Djupesland | |
| 8,171,929 B2 | 5/2012 | Djupesland et al. | |
| 8,191,552 B2* | 6/2012 | Przekwas | A61M 15/08 128/203.22 |
| 8,231,588 B2* | 7/2012 | Xia | A61M 11/06 604/187 |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2* | 10/2013 | Djupesland | A61M 11/00 128/200.23 |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2* | 3/2015 | Djupesland | A61M 15/08 128/200.14 |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| 2003/0101992 A1* | 6/2003 | Mezzoli | A61M 15/08 128/200.14 |
| 2004/0024330 A1 | 2/2004 | Djupesland et al. | |
| 2004/0112378 A1 | 6/2004 | Djupesland | |
| 2004/0112379 A1 | 6/2004 | Djupesland | |
| 2004/0112380 A1 | 6/2004 | Djupesland | |
| 2004/0149289 A1 | 8/2004 | Djupesland | |
| 2004/0182388 A1 | 9/2004 | Djupesland | |
| 2004/0238574 A1* | 12/2004 | Merk | B05B 1/267 222/321.6 |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0107957 A1 | 5/2006 | Djupesland | |
| 2006/0169278 A1 | 8/2006 | Djupesland et al. | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0289629 A1 | 11/2008 | Djupesland et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupesland | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |
| 2011/0259329 A1 | 10/2011 | Djupesland et al. | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland et al. | |
| 2012/0260915 A1 | 10/2012 | Djupesland | |
| 2013/0098362 A1 | 4/2013 | Djupesland et al. | |
| 2013/0125889 A1 | 5/2013 | Djupesland et al. | |
| 2013/0327320 A1 | 12/2013 | Djupesland | |
| 2014/0018295 A1 | 1/2014 | Djupesland | |
| 2014/0041660 A1 | 2/2014 | Djupesland et al. | |
| 2014/0060536 A1 | 3/2014 | Djupesland | |
| 2014/0073562 A1 | 3/2014 | Djupesland | |
| 2014/0144442 A1 | 5/2014 | Djupesland et al. | |
| 2014/0144443 A1 | 5/2014 | Djupesland et al. | |
| 2014/0166008 A1 | 6/2014 | Djupesland | |
| 2014/0202456 A1 | 7/2014 | Djupesland | |
| 2014/0246022 A1 | 9/2014 | Djupesland et al. | |
| 2015/0007811 A1 | 1/2015 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0090259 A1 | 4/2015 | Djupesland et al. | |
| 2015/0101605 A1 | 4/2015 | Djupesland et al. | |
| 2015/0144129 A1 | 5/2015 | Djupesland et al. | |
| 2015/0165139 A1 | 6/2015 | Hafner | |
| 2015/0182709 A1 | 7/2015 | Djupesland et al. | |
| 2015/0246194 A1 | 9/2015 | Djupesland et al. | |

(56) References Cited

U.S. PATENT DOCUMENTS

| | | |
|---|---|---|
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0310683 A1* | 10/2016 | Djupesland ........... A61M 15/08 |

FOREIGN PATENT DOCUMENTS

| | | |
|---|---|---|
| WO | WO 98/53869 | 12/1998 |
| WO | WO 1999/49984 | 10/1999 |
| WO | WO 00/51672 | 9/2000 |
| WO | WO 01/97689 | 12/2001 |
| WO | WO 2002/00282 | 1/2002 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 2003/041776 | 5/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2004/108197 | 12/2004 |
| WO | WO 2005/016423 | 2/2005 |
| WO | WO 2005/021059 | 3/2005 |
| WO | WO 2005/058400 | 6/2005 |
| WO | WO 2006/030210 | 3/2006 |
| WO | WO 2006/090149 | 8/2006 |
| WO | WO 2007/062726 | 6/2007 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

* cited by examiner

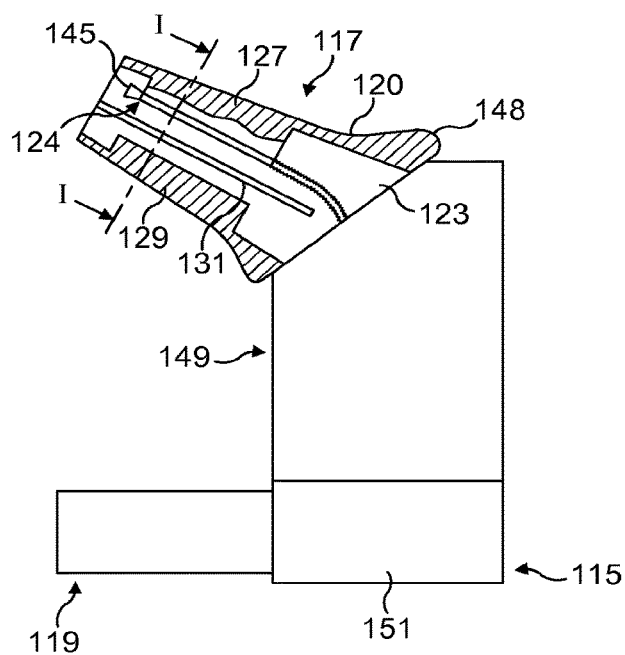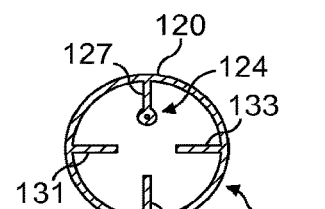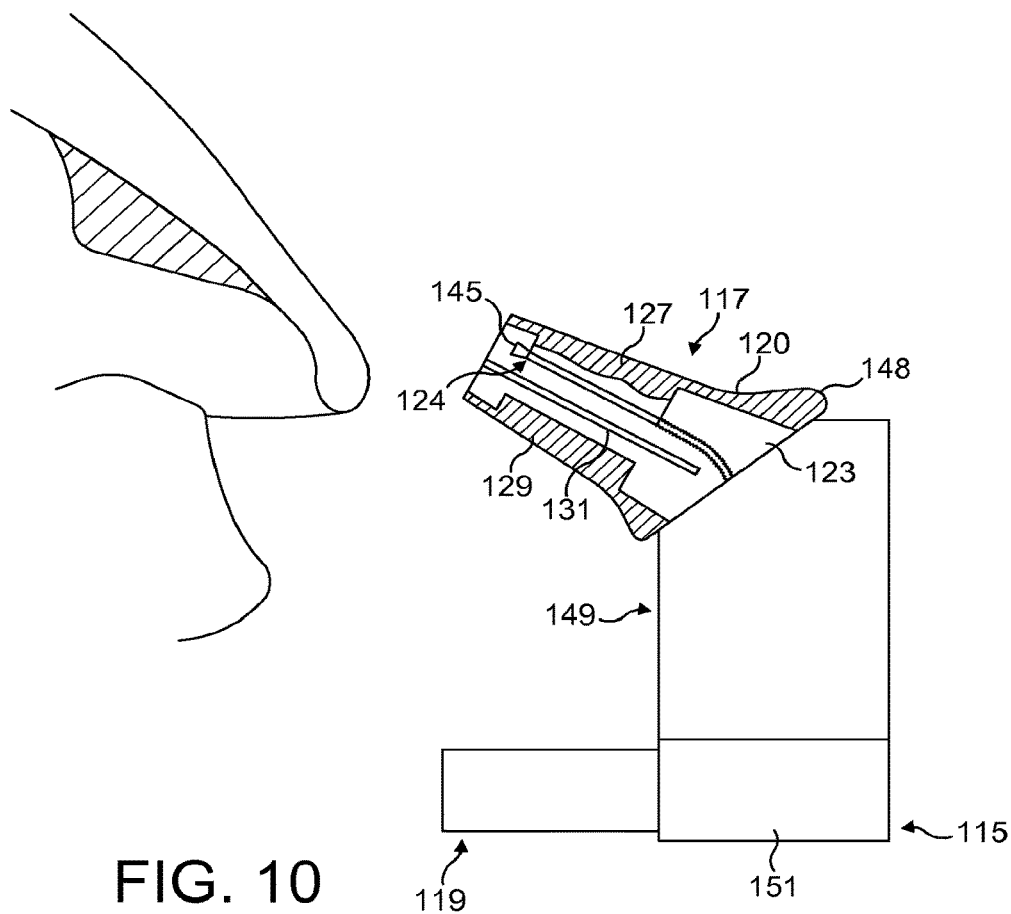

NASAL DELIVERY

CROSS REFERENCE TO RELATED APPLICATIONS

This application is a divisional application of U.S. application Ser. No. 14/047,390, filed on Oct. 7, 2013, which is a continuation application of U.S. application Ser. No. 12/281,894, filed on Jun. 12, 2009, now U.S. Pat. No. 8,550,073, which is a U.S. national phase application of PCT/IB07/01709, filed on Mar. 6, 2007, which in turn claims priority to GB 0604444.0, filed on Mar. 6, 2006.

FIELD OF INVENTION

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject.

BACKGROUND OF THE INVENTION

Referring to FIG. 1(*a*), the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

SUMMARY OF THE INVENTION

It is an aim of the present invention to provide nasal delivery devices and nasal delivery methods for providing for the improved delivery of substance to a nasal cavity of subject.

One particular aim of the present invention is to optimize the shape, direction and particle distribution of the plume of a delivered dose, in order to reach targeted regions and reduce deposition outside these regions.

Another particular aim of the present invention is to provide for improved targeting of specific regions of the nasal airway and improved reproducibility and consistency of dosing.

The present inventors have recognized that an increased delivery of substance to the posterior region of the nasal airway, and in particular the upper posterior region of the nasal airway, as illustrated in FIG. 1(b), relative to the anterior region of the nasal airway, surprisingly provides for a disproportionately greater CNS effect, which is suggestive of a greater uptake of substance into the CNS than would be predicted from the blood plasma concentration of the substance.

The posterior region of the nasal airway is that region which is posterior of the nasal valve NV, as illustrated in FIG. 1(b).

The nasal valve NV comprises the anterior bony cavum which contains inferior turbinate erectile tissue and septal erectile tissue, which are supported respectively by compliant ala tissue and the rigid cartilaginous septum (Cole). These elements combine to form a dynamic valve, which extends over several millimeters, that adjusts nasal airflow, and is stabilized by cartilage and bone, modulated by voluntary muscle and regulated by erectile tissue. The lumen of the nasal valve NV is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve NV is lined in its anterior part with transitional epithelium, with a gradual transition posterior to respiratory epithelium. The nasal valve NV and anterior vestibule define roughly the anterior one-third of the nose.

In human subjects, the upper lateral wall of the nasal valve NV collapses to form a collapsed region, as illustrated in FIG. 1(b), which significantly narrows the upper part of the nasal valve NV and obstructs access to the upper posterior region of the nasal cavity, and in particular the olfactory region. This collapsed region, in combination with the upper lateral wall of the nasal valve NV having a curved shape, makes the insertion of a rigid structure into the lumen of the nasal valve NV particularly difficult and uncomfortable.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 1(b), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1(b), the posterior region of the nasal airway is the nasal region posterior of an imaginary vertical plane VERT which is located at a position corresponding to the lower angle of the anterior nasal aperture (aperture piriformis), which corresponds substantially to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger defines the distance between the anterior nasal spine AnS and the posterior nasal spine PnS as being 56 mm in eighteen year old boys and 53.3 mm in eighteen year old girls).

As further illustrated in FIG. 1(b), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al define the distance from the nasal floor NF to the cribiform plate CP as 46+/−4 mm).

The upper posterior region is thus that upper posterior region which is bounded by the above-defined vertical and horizontal planes VERT, HORIZ.

The present inventors have postulated that this increased concentration within the CNS arises as a result of the veins in the upper posterior region of the nasal airway draining backwards to the venous sinuses that surround the brain, which leads to a higher local concentration in the cerebrovasculature. Although the sinus cavernous is outside the blood-to-brain barrier, animal models have shown that substances can be transported by a counter-current mechanism from the veins therein to the carotid artery which passes through the sinus cavernous. Other mechanisms have been proposed which include extra axonal transport along the surface of the olfactory and trigeminal nerves. This mode of transport is apparently quite rapid as compared to intra axonal transport.

The improved efficacy as achieved by the present invention as compared to existing nasal spray administration systems can apparently be explained in that such nasal spray administration systems have been determined initially to deliver largely to the anterior one-third of the nasal airway, that is, the nasal region anterior of the nasal valve, from which region drainage is mainly along the floor of the nose and in which region the veins drain to the external facial vein, which in turn drains to the external carotid and in turn to the peripheral circulation.

In one aspect the present invention provides a nosepiece which provides for expansion in the sagittal plane, opening the connection of the mucosal surfaces of the nasal valve and isthmus, in particular by expansion of the collapsed region at the upper lateral wall of the nasal valve.

In another aspect the present invention provides a nosepiece which includes a flexible tip to fit the cross-sectional shape of a nasal cavity. In a preferred embodiment the nosepiece has an internal configuration, at least at the tip, which acts to prevent collapse and maintain a stable cross-sectional area and a relatively-stable resistance.

In a further aspect the present invention provides a spray nozzle which provides an asymmetrical spray plume, where either a powder or a liquid.

The present invention is particularly advantageous when used in combination with bi-directional nasal delivery, but is not restricted to such delivery.

The present invention can be combined with delivery concepts which generate a mist, an aerosol, an aerosol spray of particles, either liquid or powder, drops, droplets, or a liquid jet or jets of liquid.

An entraining flow can be provided by the exhalation breath of the subject or from an external flow source, such as from an air chamber or a compressed air supply.

The delivery device can be triggered, such that one or both of the dose and gas flow are triggered by an intraoral pressure which is such as to close the oropharyngeal velum or by another event, which may or may not secure velum closure.

The present invention also finds application in delivery systems which do not utilize an auxiliary gas flow and even with inhalation environments which provide for nasal inhalation or a sniffing manoeuvre through one or both of the nostrils.

The devices can be a multi-dose or single-dose.

Preliminary results in models and gamma-scintigraphic pilot studies show that it is possible to improve the access to and deposition in the narrow passages of the upper region of the nasal airway including the olfactory region, the regions with veins draining to the sinus cavernous and innervated by the trigeminal nerve.

Furthermore, experiments in models and humans show that modification of the plume geometry and positioning of the nozzle provides for optimal delivery.

U.S. Pat. No. 6,647,980 discloses a device which utilizes a modified plume in order to attempt to decrease lateral deposition, and thereby increase the amount of the dose which reaches the upper region of the nasal airway. Although this device may provide for reduced deposition in the anterior part of the nasal cavity which is lined by squamous epithelium, owing to the narrower cone angle, only a moderate increase in deposition in the upper region of the nose is expected to be achieved, owing to the difficult and protected access to this region. Furthermore, narrowing of the nose during inhalation, as caused by the Bernoulli effect, will further narrow the nasal cavity to increase the fraction deposited in valve region.

In its preferred embodiment the present invention provides for a bi-directional air flow in the nasal passages in which optimally-sized particles are entrained and subsequently delivered to appropriate target sites in the nasal airway.

The present invention aims further to improve upon the devices as disclosed in the applicant's earlier WO-A-03/000310, the content of which is herein incorporated by reference.

In one embodiment the present invention provides for optimisation of the delivery to upper parts of the nasal airway, including the olfactory region, by configuring the nosepiece, in particular the shape and position thereof, and the emitted plume of particles or liquid jet or jets in conjunction.

In one embodiment the present invention provides for significantly enhanced access and deposition in the upper region of the nasal airway, and thereby improved dose-to-dose consistency and repeatability of drug delivery to this region of the nasal airway.

In one embodiment the present invention provides for expansion of the nasal airway in the vertical or sagittal plane and the delivery of an asymmetric plume which has the greater spray angle in the vertical plane, and this particular mode of expansion of the nasal airway in combination with the particular geometrical arrangement of the spray plume has been found to be particularly advantageous in achieving targeted delivery to posterior regions, in particular the olfactory region, of the nasal airway.

The delivery device of the present invention provides both for positioning of the outlet nozzle and the expansion of the upper lateral and medial surfaces of the valve region of a nasal cavity.

By configuring the external and internal shape of the nosepiece, the nosepiece both ensures the correct positioning of the outlet nozzle and optimizes the vertical expansion of the nasal cavity.

The operative function of the nosepiece of the present invention, in vertically expanding the nasal cavity, can be contrasted to that of a conventional, frusto-conical nosepiece, which, during insertion into a nasal cavity, has been found by the present inventor to push the soft, nasal tissue rearwardly, which is particularly disadvantageous where attempting delivery to posterior regions of the nasal airway. One such nosepiece is disclosed in WO-A-1999/049984.

Various other nosepiece geometries are known for nasal delivery devices, such as disclosed in US-A-2003/0101992, U.S. Pat. No. 6,561,193 and WO-A-2004/108197, but none of these nosepieces are configured to provide for vertical or sagittal expansion of the nasal cavity, in particular at the nasal valve.

In its preferred embodiment the present invention provides a narrow nosepiece which can be easily slid into a nasal cavity beyond the nasal valve to the required depth, before expansion in the vertical or sagittal plane.

This expanding movement of the nosepiece can either be to the upper part, the lower part or both the upper and lower parts.

In one embodiment the nosepiece comprises two members, that is, an upper and a lower member, where one or both of the members are movable relative to the supporting body. Such members are exemplified by a pair of scissors, a pair of pliers and expansion screws.

In another embodiment the nosepiece could comprise an expanding cuff-like member, which comprises one or both of upper and lower cuff members which expand in the vertical plane.

In one embodiment the nosepiece can comprise a moderately-flexible anterior part such as to allow the nosepiece to adapt to the curved shape of a nasal passage, and thereby facilitate deeper insertion into the nasal slit, and even into the bony part thereof.

In a preferred embodiment the nosepiece includes internal features, such as ribs, which prevent collapse of the flow path and prevents substantial reduction in the internal cross-sectional area, which would otherwise lead to an increase in flow resistance.

This flexibility enables the nosepiece to conform, at least in part, to the different shapes and directions of the nasal passage in this region, but at the same time assists in expanding the isthmus. Though the shape of the anterior part of the nasal passage normally varies within a pre-defined range, pathological deviations may cause more pronounced changes which otherwise may create problems for insertion and positioning of the nosepiece, and hence efficient delivery.

Furthermore, this adaptation of the anterior shape of the nosepiece to conform to the nasal passage provides for reduced turbulence, which would otherwise lead to unwanted deposition in the zone of turbulence.

The present invention also provides for a nozzle, such as the swirl chamber of a spray pump or a pMDI or a nebulizer, which delivers a modified, asymmetric plume of particles.

In its preferred embodiment the plume is an asymmetric plume which is relatively flat, with a small dimension in one axis and much greater in the other axis.

Such a shaped plume reduces deposition in the anterior part of the valve region and increases the fraction of the dose entering into the upper, more posterior region of the nasal passage including the olfactory region and the sinus ostia, which is located below the middle meatus.

The present invention also extends to means for securing a correct and reproducible positioning of nosepiece.

Positioning of the delivery device can be achieved by the function of the mouthpiece or an exit resistor in the exit nostril of a bi-directional device, or as a separate feature with the main function of assisting positioning of the nosepiece. Triangular-shaped nose pieces assist in achieving the correct positioning. The mouthpiece of a device intended for bi-directional delivery also assists in achieving a reproducible positioning of the nosepiece. The provision of a nosepiece in the contralateral nostril also assists in achieving a reproducible positioning of the nosepiece. The provision of a special cap or the like as applied to the exterior of the exterior nose also assists in achieving a reproducible positioning of the nosepiece. Also, tape or vacuum can be used to assist in positioning of the nosepiece and potentially in addition helps expanding the valve region by external action, such as an external dilator used to open the nose ("Breath-Right" nasal strip).

The present invention extends to devices which are adapted to bi-directional delivery where driven by the exhalation breath of the subject or an auxiliary gas source, and conventional nasal delivery devices which do not utilize an auxiliary gas flow.

Furthermore, the present invention can be adapted to any traditional delivery modality, including but not restricted to a spray pump, a pMDI, a nebulizer or any other means of delivering liquid jets, particles or drops, either in powder or liquid form.

In its preferred embodiment the present invention provides for expansion in the vertical or sagittal plane, but the expansion is not restricted to this plane. The expansion can be a combination of movement in different planes.

The expansion can be only or predominantly to the upper part or the lower part of a nasal cavity, or the upper and lower parts in combination.

The expansion can be achieved by any possible movement, such as pushing, pulling, lifting, pressing, rotating, expanding, flexing, suction (vacuum) and even by secondary chemical reactions initiated by, for example, pressure, moisture and temperature which create the desired movement of retraction of a mass or volume.

In one embodiment, where the nosepiece comprises two movable members in the form of a speculum, one of the members can provide a delivery channel through which substance is delivered into the nasal airway, and the other member can include a pressure-sensitive release valve or an open channel which allows for the venting of particles from the nasal airway. Such a configuration has particular application in relation to a completely obstructed nose, where the delivered flow would otherwise have no means of escape.

Where the substance includes relatively-large particles, those particles will due to their momentum travel forward and deposit on an opposing surface, whereas the air flow will deviate and flow towards the exit valve.

In having an on/off valve which opens at a predetermined pressure which is just above the pressure where bi-directional flow is expected to occur in a moderately-blocked nose, an air flow will occur suddenly and carry the particles forward, and this will entrain the particles or at least a large fraction of the particles into the blocked nose and onto an opposing surface before the airflow turns around and exits in the opposite direction through the valve.

The valve can have a filter to prevent the particles from escaping to the atmosphere. Using large particles, such as from about 100 μm to about 200 μm, will also avoid or at least reduce this problem.

By providing a relatively-large distance between the point of emission, which is preferably in the upper member, and the point of exit, which is preferably in the lower arm, increased deposition can be achieved.

In a preferred embodiment the positioning of the nosepiece should preferably occur prior to release of substance, but could also occur in sequence immediately prior to or simultaneously with the releasing action.

The preferred action is as follows. The positioning and expansion of the specialized nozzle can be achieved by a finger action. When complete, this action will also open the flow path permitting delivery of substance into the nasal airway, preferably by bi-directional delivery, but alternatively also even in the absence of bi-directional delivery. Alternatively, a pre-charged spring or similar can be released when the nosepiece is inserted into a nostril to the correct position. When this positioning action is complete, a valve is opened, making it possible to blow through the device or alternatively release the force from a gas chamber or another stored force, or alternatively allowing a mechanical action by hand compression, similar to actuation of a spray pump. In an alternative configuration, which can be utilized with or without bi-directional flow, for example, when used in infants and unconscious subjects, the two actions of expansion and release of substance from, for example, a spray pump can be integrated. The first part of the mechanical action/compression of a lever by the finger will secure the expansion of the lever and positioning of the nosepiece. Then, when a certain trigger point or resistance is reached the finger force will result in the generation of a spray or release of a compressed gas by exhalation against a resistor or from a pressurized compartment or the combination thereof.

The following represent potential areas of application. Delivery to the olfactory epithelium for transport into or along nerve paths or by diffusion across the cribiform plate. Delivery to the upper part of the nasal passage including the olfactory region which drains via veins to the sinus cavernous to achieve higher concentrations of drugs, with the potential of diffusing into the carotid artery passing through the sinus cavernous, where diffusing through the rete mirabile. Delivery to the branches of the trigeminal nerve for potential peripheral action on the nerves (anagetic), uptake and transport along the nerves to the central ganglion and potentially into the CNS or with reflectory actions in other parts of the face or CNS. Deposition of drugs in the middle meatus and infundibulum which includes the sinus ostia. This region plays a key role in ventilation of the sinuses and in the development of sinus pathology and consequently for the treatment of pathology in this region. Delivery of topically-acting substances, such as decongestants, steroids and antihistamines, which can reduce the mucosal swelling in the entrances to and in the narrow slit like passages of the upper part of the nose in order to improve olfaction or reverse anosmia.

BRIEF DESCRIPTION OF THE DRAWINGS

Preferred embodiments of the present invention will now be described hereinbelow by way of example only with reference to the accompanying drawings, in which:

FIG. 8 illustrates a nasal delivery device in accordance with a second embodiment of the present invention;

FIG. 9 illustrates a cross sectional view (along section I-I in FIG. 8) of the nosepiece assembly of the delivery device of FIG. 8;

FIG. 10 illustrates the delivery device of FIG. 8 prior to insertion into a nasal cavity of a subject;

DETAILED DESCRIPTION OF EMBODIMENTS

Figure 1A:
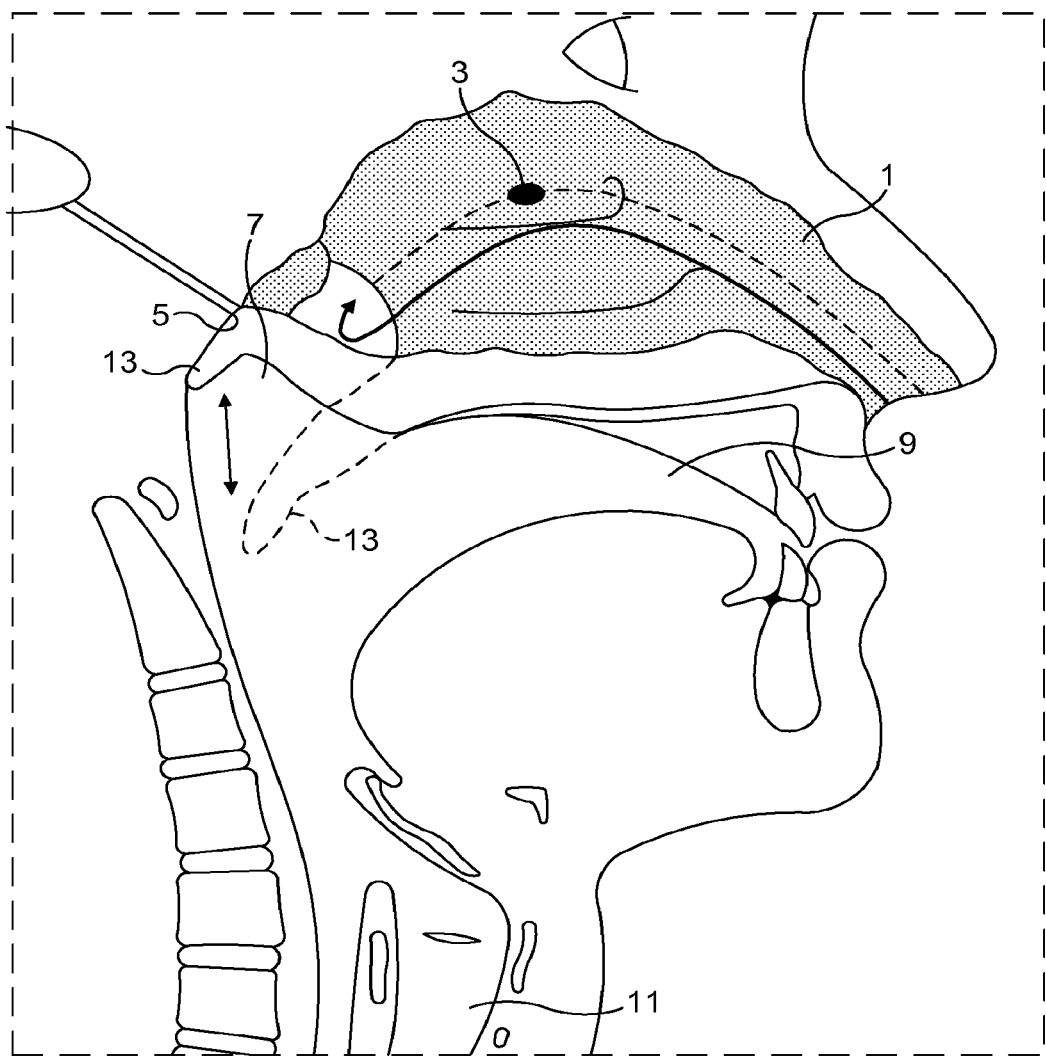
FIG. 1(a) schematically illustrates the anatomy of the upper respiratory tract of a human subject.
Figure 1B:
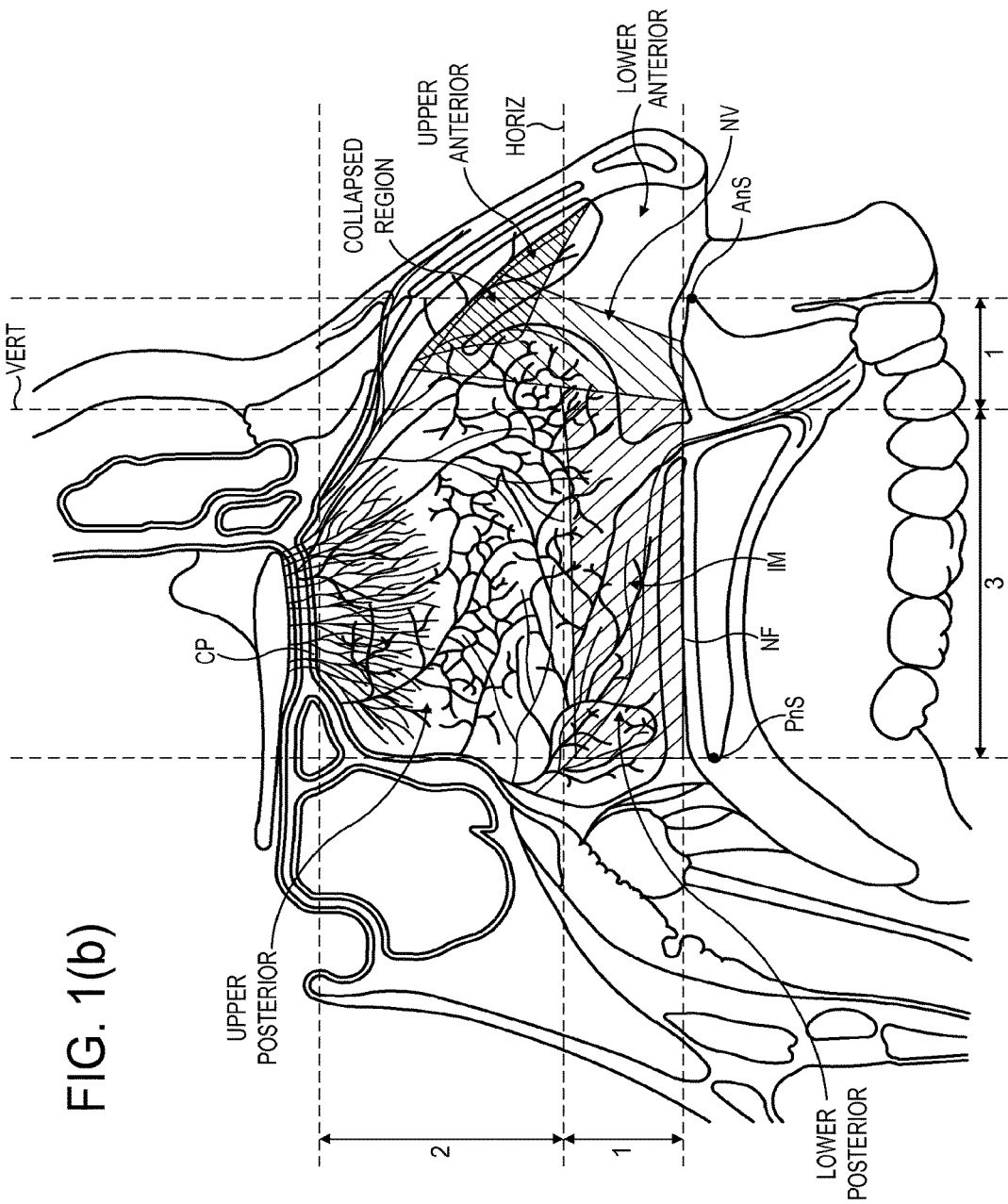
FIG. 1(b) illustrates the segmentation of a nasal cavity in accordance with a preferred embodiment of the present invention.
Figure 2:
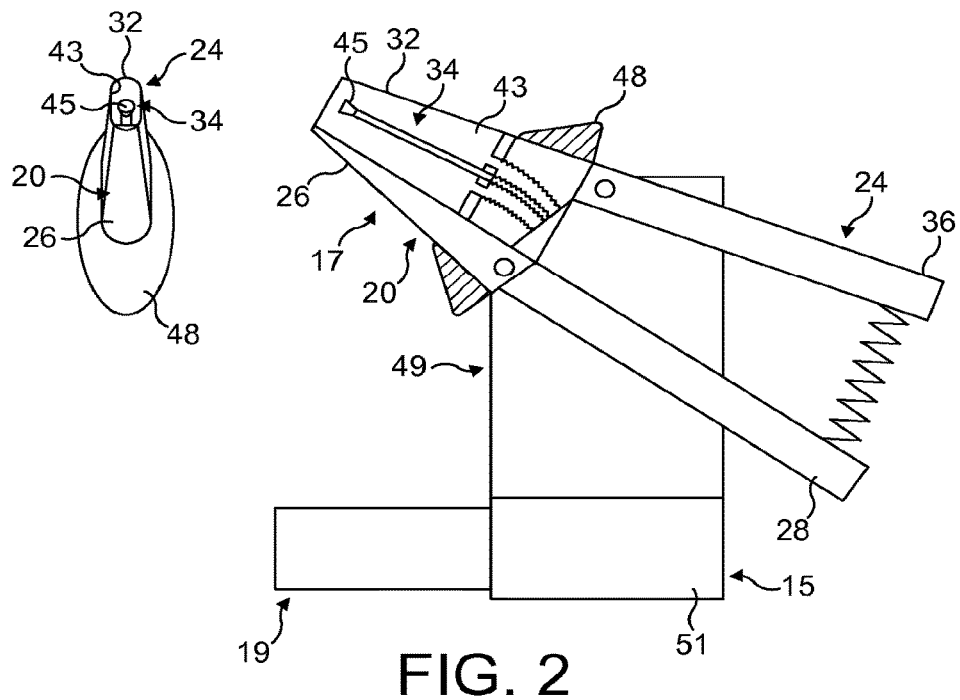
FIG. 2 illustrates a nasal delivery device in accordance with a first embodiment of the present invention.

FIGS. 2 to 6 illustrate a nasal delivery device in accordance with a first embodiment of the present invention.

The delivery device comprises a housing 15, a nosepiece assembly 17 for fitting in a nasal cavity of a subject, and a mouthpiece unit 19 through which the subject exhales to actuate the delivery device.

The nosepiece assembly 17 comprises first and second nosepiece units 20, 24 which are movably coupled, in this embodiment pivotally coupled, to the housing 15 and are operable by the subject, in this embodiment by gripping the same between one of the fingers and the thumb, to expand the nasal cavity of the subject in the vertical or sagittal plane.

In this embodiment the first nosepiece unit 20 comprises a lower, guide element 26 which acts to guide the nosepiece assembly 17 when fitted in the nasal cavity of the subject, and an actuating arm 28 which extends rearwardly of the guide element 26 and is operated by the subject, in this embodiment by gripping the same, to position the guide element 26.

In this embodiment the second nosepiece unit 24 comprises an upper, delivery element 32 which acts to guide the nosepiece assembly 17 when fitted in the nasal cavity of the subject, an outlet unit 34 which is disposed within the delivery element 32 for delivering substance into the nasal airway of the subject, and an actuating arm 36 which extends rearwardly of the delivery element and is operated by the subject, in this embodiment by gripping the same, to position the delivery element 32.

In this embodiment the delivery element 32 has a relatively-narrow section in the horizontal plane so as to facilitate insertion beyond the narrow nasal valve of the nasal cavity of the subject and a tapering section in the vertical plane which narrows to the distal end thereof.

In this embodiment the outlet unit 34 comprises a delivery channel 43 which is in fluid communication with the mouthpiece unit 19 such that an air flow is delivered into and through the nasal airway of the subject on exhalation by the subject through the mouthpiece unit 19, and a nozzle 45 for delivering substance to the nasal airway of the subject.

In this embodiment the nozzle 45 is disposed in the delivery channel 43 co-axially with the same.

In this embodiment the nozzle 45 is configured to provide an aerosol spray.

In an alternative embodiment, for the delivery of a liquid, the nozzle 45 could be configured to deliver a liquid jet as a column of liquid.

In this embodiment the outlet unit 34 is coupled to the housing 15 by a flexible coupling, such as to allow for the positioning of the delivery element 32 in the nasal cavity of the subject, as will be described in more detail hereinbelow.

In an alternative embodiment the delivery element 32 could be fixed to the housing 15, and the mouthpiece unit 19 instead movably coupled to the housing 15, typically by a flexible coupling, such as to allow for the positioning of the delivery element 32 in the nasal cavity of the subject.

Figure 7A:
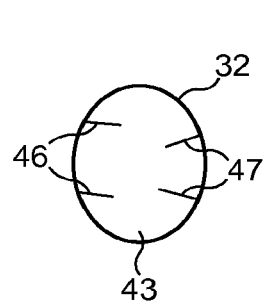
FIGS. 7(a) and (b) illustrate the tip of a delivery element as one modified embodiment of the delivery device of FIG. 2, where illustrated in respective ones of the rest or uncompressed state and the operative or compressed state.
Figure 7B:
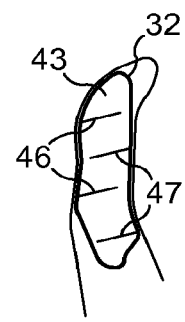

In one embodiment, as illustrated in FIGS. 7(a) and (b), at least the tip of the delivery element 32 can comprise a tubular section of a flexible, preferably resilient, material, which is such as to expand in the vertical axis when compressed in the horizontal axis. In a preferred embodiment the material is a semi-soft plastics material, such as silicone rubber.

In this embodiment the tip of the delivery element 32 is configured such that the lateral sections thereof preferentially flex when compressed in the horizontal axis, but yet exhibit sufficient rigidity as to drive the upper and lower sections thereof to expand in the vertical axis.

In this embodiment the tip of the delivery element 32 includes supporting elements 46, 47 which are disposed to the inner surface at the lateral sections of the tip of the delivery element 32, and act to prevent compression of the lateral sections of the tip of the delivery element 32 beyond a predetermined separation, which is that required to achieve an optimal flow profile through the nosepiece 120.

With this configuration, as will be described in more detail hereinbelow, operation of the actuating arms 28, 36 of the first and second nosepiece units 20, 24, in this embodiment by gripping the same between ones of the fingers and the thumb, causes the expansion of the guide element 26 of the first nosepiece unit 20 relative to the delivery element 32 of the second nosepiece unit 24 to an expanded state.

This expansion acts to engage the lower and upper walls of the nasal cavity of the subject and cause the expansion of the nasal cavity in the vertical plane, in particular the upper wall of the nasal cavity of the subject, which is a fleshy structure as compared to the lower wall of the nasal cavity of the subject, which is a relatively-firm structure, and also position the delivery element 32 of the second nosepiece unit 24 in the nasal cavity of the subject, with the lower wall of the nasal cavity of the subject, in being a relatively-hard structure, acting as a reference for the expansion.

This expansion further acts to tension the lateral walls of the nasal cavity of the subject which defines the nasal valve, which causes the lateral walls of the nasal cavity to be urged into sealing contact with the delivery element 32 of the second nosepiece unit 24.

In this embodiment the nozzle 45 of the outlet unit 34 is configured to deliver an asymmetric aerosol spray, with the aerosol spray having a significantly greater spray angle in the vertical plane α than in the horizontal plane β. Such an aerosol spray has been found to be particularly advantageous in the delivery of substance to posterior regions of the nasal cavities, in particular the olfactory region. In a preferred embodiment the spray angle in the vertical plane α is greater than 35°, and more preferably greater than 40°.

In this embodiment the aerosol spray presents an elliptical spray zone.

In another embodiment the aerosol spray could present a substantially rectangular spray zone.

The nosepiece assembly 17 further comprises a sealing member 48, in this embodiment a tapered, annular ring of a resilient material, which acts both to provide a seal with the nares of the nostril of the nasal cavity of the subject and determine the extent of the insertion of the outlet unit 34 of the second nosepiece unit 24 of the nosepiece assembly 17 into the nasal cavity of the subject. In a preferred embodiment the distal end of the outlet unit 34 is configured to extend at least about 2 cm, preferably at least about 3 cm, more preferably at least about 4 cm, and preferably from about 2 cm to about 4 cm, into the nasal cavity of the subject.

The delivery device further comprises a substance supply unit 49 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 45 of the outlet unit 34 to deliver substance from the nosepiece assembly 17, in this embodiment as an aerosol spray.

In this embodiment the substance supply unit 49 is a multi-dose unit for delivering a plurality of metered doses of substance. In another embodiment the substance supply unit 49 could be a single-dose unit for delivering a single metered dose of substance.

The substance supply unit 49 is pre-primeable, in this embodiment by loading a resilient element, and includes a breath-actuated release mechanism 51 which, when triggered, releases the resilient element and actuates the substance supply unit 49 to deliver a metered dose of substance through the nozzle 45 of the outlet unit 34.

In this embodiment the release mechanism 51 is configured to cause actuation of the substance supply unit 49 on generation of a predetermined flow rate through the delivery channel 43 of the delivery element 32.

In another embodiment the release mechanism 51 could be configured to cause actuation of the substance supply unit 49 on generation of a predetermined pressure within the delivery channel 43 of the delivery element 32.

In a further embodiment the release mechanism 51 could be configured to cause actuation of the substance supply unit 49 on generation of either one of a predetermined flow rate through the delivery channel 43 of the delivery element 32 or a predetermined pressure within the delivery channel 43 of the delivery element 32.

In an alternative embodiment the substance supply unit 49 could comprise a mechanical delivery pump, in particular a liquid delivery pump or a powder delivery pump, which delivers metered doses of a substance on actuation thereof.

In another alternative embodiment the substance supply unit 49 could comprise a dry powder delivery unit which delivers metered doses of a substance, as a dry powder, on actuation thereof.

In yet another alternative embodiment the substance supply unit 49 could comprise a nebulizer which delivers metered doses of a substance, as an aerosol spray, on actuation thereof.

Operation of the delivery device will now be described hereinbelow with reference to FIGS. 3 to 6 of the accompanying drawings.

Figure 3:
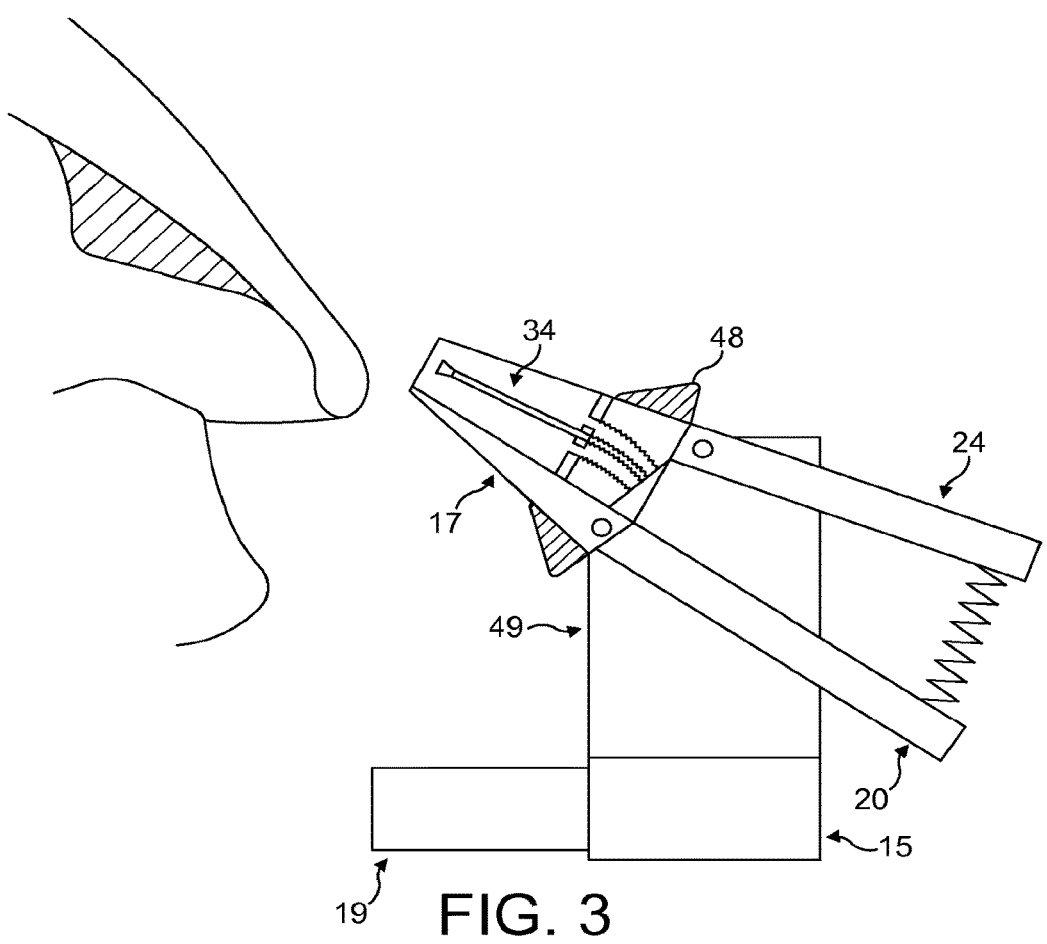
FIG. 3 illustrates the delivery device of FIG. 2 prior to insertion into a nasal cavity of a subject.
Figure 4:
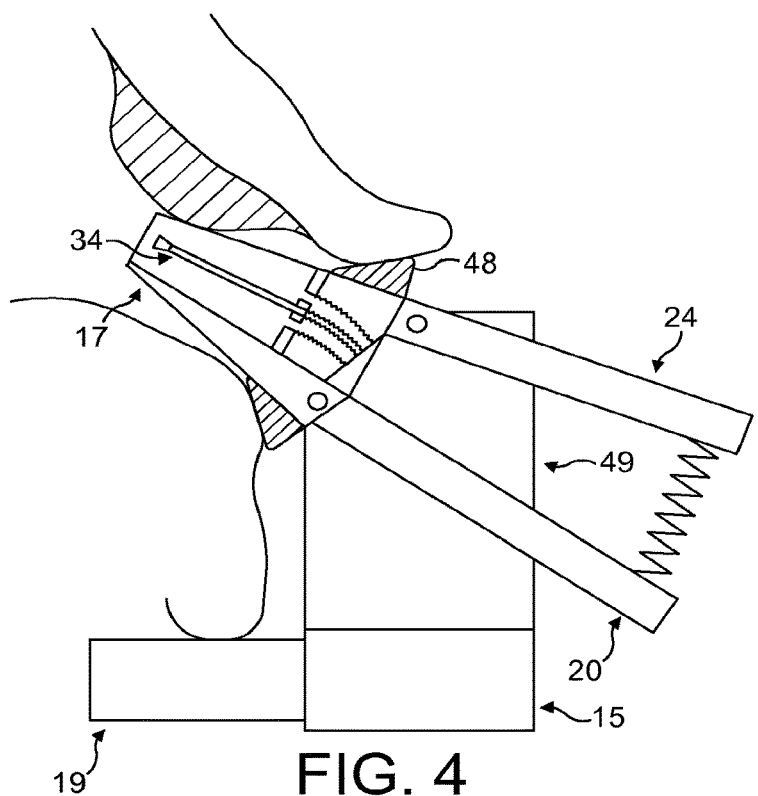
FIG. 4 illustrates the delivery device of FIG. 2 inserted into a nasal cavity of the subject prior to operation.

Referring to FIGS. 3 and 4, the nosepiece assembly 17 is first inserted into one of the nasal cavities of a subject until the sealing member 48 abuts the nares of the nostril of the subject, at which point the distal end of the outlet unit 34 typically extends from about 2 cm to about 4 cm into the nasal cavity of the subject, and the mouthpiece unit 19 is then gripped in the lips of the subject.

Figure 5:
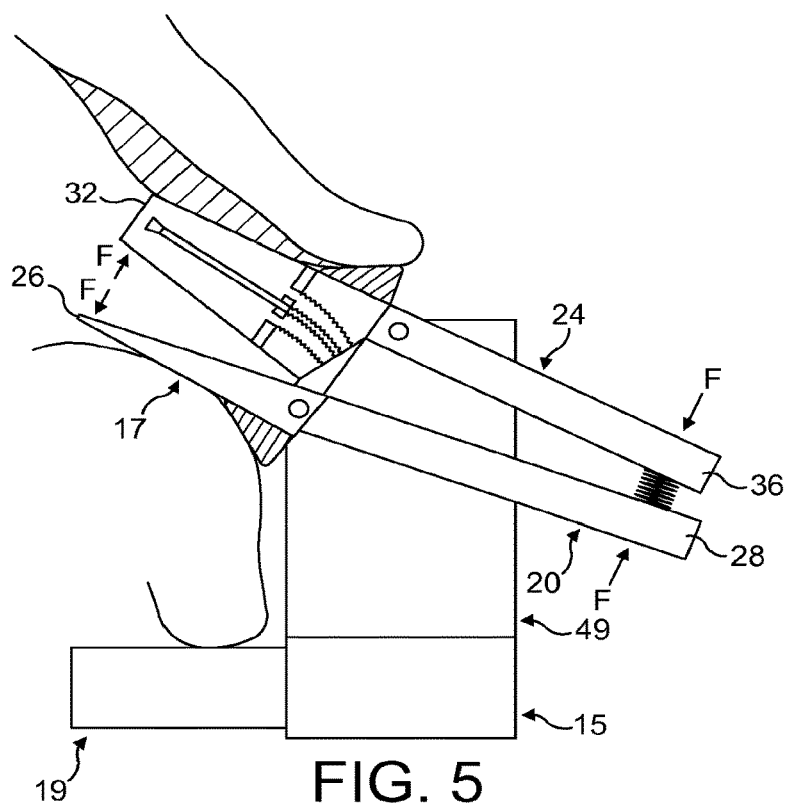
FIG. 5 illustrates the delivery device of FIG. 2 following operation of the actuating members of the nosepiece assembly to expand the upper and lower walls of the nasal cavity of the subject.

Referring to FIG. 5, the subject then operates the actuating arms 28, 36 of the first and second nosepiece units 20, 24, in this embodiment by gripping the same between ones of the fingers and the thumb, to cause the expansion of the guide element 26 of the first nosepiece unit 20 relative to the delivery element 32 of the second nosepiece unit 24 to an expanded state. This expansion acts to engage the lower and upper walls of the nasal cavity of the subject and cause the expansion of the nasal cavity in the vertical plane, in particular the upper wall of the nasal cavity of the subject, which is a fleshy structure, as compared to the lower wall of the nasal cavity of the subject, which is a relatively-hard structure, and position the delivery element 32 of the second nosepiece unit 24 in the nasal cavity of the subject, with the lower wall of the nasal cavity of the subject being a relatively-hard structure, which acts as a reference for the expansion. This expansion also acts to tension the lateral walls of the nasal cavity of the subject which defines the nasal valve, which causes the lateral walls to be urged into sealing contact with the delivery element 32 of the second nosepiece unit 24.

Figure 6:
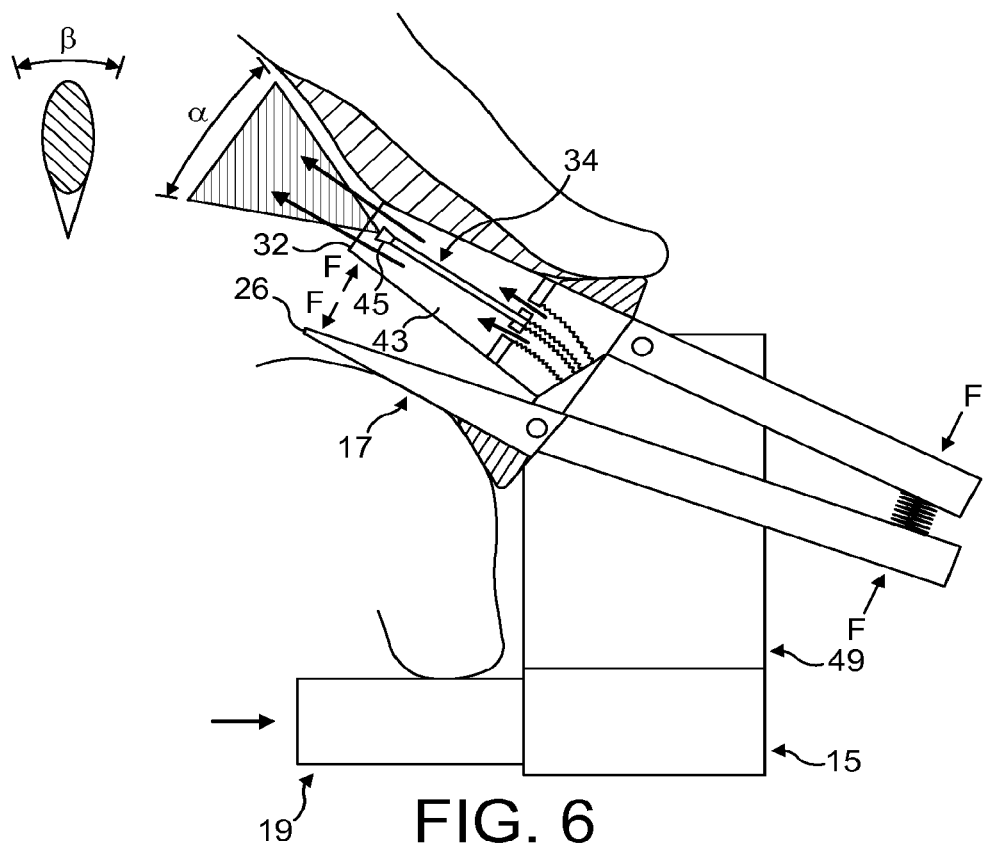
FIG. 6 illustrates the delivery device of FIG. 2 following actuation of the substance supply unit.

Referring to FIG. 6, the subject then begins to exhale through the mouthpiece unit 19, which exhalation acts to close the oropharyngeal velum of the subject and drive an air flow through the delivery channel 43 of the outlet unit 34, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 43 of the delivery element 32 reaches a predetermined value, the release mechanism 51 is triggered to actuate the substance supply unit 49 to deliver a metered dose of a substance to the nozzle 45 of the outlet unit 34 and into the nasal cavity of the subject, in this embodiment as an asymmetric aerosol spray. In the alternative embodiment the release mechanism 51 could be triggered on the generation of a predetermined pressure in the delivery channel 43 of the delivery element 32.

Following exhalation, the subject then releases the actuating arms 28, 36 of the first and second nosepiece units 20, 24, which causes the guide element 26 of the first nosepiece unit 20 and the delivery element 32 of the second nosepiece unit 24 to return to the contracted state, at which point the mouthpiece unit 19 is released and the nosepiece assembly 17 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 49.

FIGS. 8 to 13 illustrate a nasal delivery device in accordance with a second embodiment of the present invention.

The delivery device comprises a housing 115, a nosepiece assembly 117 for fitting in a nasal cavity of a subject, and a mouthpiece unit 119 through which the subject exhales to actuate the delivery device.

The nosepiece assembly 117 comprises a nosepiece 120 which is attached to the housing 115 and defines a delivery channel 123 which is in fluid communication with the mouthpiece unit 119 such that an air flow is delivered into and through the nasal airway of the subject on exhalation by the subject through the mouthpiece unit 119, and an outlet unit 124 which is disposed within the nosepiece 120 for delivering substance into the nasal airway of the subject.

In this embodiment the nosepiece 120 is frusto-conical in shape and semi-flexible, here formed of a semi-soft plastics material, such as to expand in the vertical axis when compressed in the horizontal axis.

In this embodiment the nosepiece 120 is configured such that the lateral sections thereof preferentially flex when compressed in the horizontal axis, but yet exhibit sufficient rigidity as to drive the upper and lower sections thereof to expand in the vertical axis.

In this embodiment the nosepiece 120 includes upper and lower re-inforcing elements 127, 129 which are disposed to the inner surface at the upper and lower sections of the nosepiece 120, and provide for the application of the expansion force to upper and lower regions of the nasal cavity of the subject.

In this embodiment the nosepiece 120 includes supporting elements 131, 133 which are disposed to the inner surface at the lateral sections of the nosepiece 120, and act to prevent compression of the lateral sections of the nosepiece 120 beyond a predetermined separation, which is that required to achieve an optimal flow profile through the nosepiece 120.

In this embodiment the outlet unit 124 comprises a nozzle 145 for delivering substance to the nasal airway of the subject. In this embodiment the nozzle 145 is disposed to the upper re-inforcing element 127. In this embodiment the nozzle 145 is configured to provide an aerosol spray. In an alternative embodiment, for the delivery of a liquid, the nozzle 145 could be configured to deliver a liquid jet as a column of liquid.

In this embodiment the outlet unit 124 is coupled to the housing 115 by a flexible coupling, such as to allow for the positioning of the nosepiece 120 in the nasal cavity of the subject, as will be described in more detail hereinbelow.

With this configuration, as will be described in more detail hereinbelow, insertion of the nosepiece 120 into the nasal cavity of the subject acts to compress the lateral sections of the nosepiece 120 by engagement with the relatively-narrow passage as presented at the nasal valve, which in turn acts to cause the expansion of the upper and lower sections of the nosepiece 120 in the vertical axis.

This expansion acts to engage upper and lower walls of the nasal cavity of the subject and cause the expansion of the nasal cavity in the vertical plane, in particular the upper wall of the nasal cavity of the subject, which is a fleshy structure, as compared to the lower wall of the nasal cavity of the subject, which is a relatively-hard structure, and also position the nosepiece 120 in the nasal cavity of the subject, with the lower wall of the nasal cavity of the subject, in being a relatively-hard structure, acting as a reference for the expansion.

This expansion further acts to tension the lateral walls of the nasal cavity of the subject which defines the nasal valve, which causes the lateral walls of the nasal cavity to be urged into sealing contact with the nosepiece 120.

In this embodiment the nozzle 145 of the outlet unit 124 is configured to deliver an asymmetric aerosol spray, with the aerosol spray having a significantly greater spray angle in the vertical plane $\alpha$ than in the horizontal plane $\beta$. Such an aerosol spray has been found to be particularly advantageous in the delivery of substance to posterior regions of the nasal cavities, in particular the olfactory region. In a preferred embodiment the spray angle in the vertical plane $\alpha$ is greater than 35°, and more preferably greater than 40°.

In this embodiment the aerosol spray presents an elliptical spray zone.

In another embodiment the aerosol spray could present a substantially rectangular spray zone.

The nosepiece assembly 117 further comprises a sealing member 148, in this embodiment a tapered, annular ring of a resilient material, which acts both to provide a seal with the nares of the nostril of the nasal cavity of the subject and determine the extent of the insertion of the outlet unit 124 of the nosepiece assembly 117 into the nasal cavity of the subject. In a preferred embodiment the distal end of the outlet unit 124 is configured to extend at least about 2 cm, preferably at least about 3 cm, more preferably at least about 4 cm, and preferably from about 2 cm to about 4 cm, into the nasal cavity of the subject.

The delivery device further comprises a substance supply unit 149 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 145 of the outlet unit 124 to deliver substance from the nosepiece assembly 117, in this embodiment as an aerosol spray.

In this embodiment the substance supply unit 149 is a multi-dose unit for delivering a plurality of metered doses of substance. In another embodiment the substance supply unit 149 could be a single-dose unit for delivering a single metered dose of substance.

The substance supply unit 149 is pre-primeable, in this embodiment by loading a resilient element, and includes a breath-actuated release mechanism 151 which, when triggered, releases the resilient element and actuates the substance supply unit 149 to deliver a metered dose of substance through the nozzle 145 of the outlet unit 124.

In this embodiment the release mechanism 151 is configured to cause actuation of the substance supply unit 149 on generation of a predetermined flow rate through the delivery channel 123 of the nosepiece 120.

In another embodiment the release mechanism 151 could be configured to cause actuation of the substance supply unit 149 on generation of a predetermined pressure within the delivery channel 123 of the nosepiece 120.

In a further embodiment the release mechanism 151 could be configured to cause actuation of the substance supply unit 149 on generation of either one of a predetermined flow rate through the delivery channel 123 of the nosepiece 120 or a predetermined pressure within the delivery channel 123 of the nosepiece 120.

In an alternative embodiment the substance supply unit 149 could comprise a mechanical delivery pump, in particular a liquid delivery pump or a powder delivery pump, which delivers metered doses of a substance on actuation thereof.

In another alternative embodiment the substance supply unit 149 could comprise a dry powder delivery unit which delivers metered doses of a substance, as a dry powder, on actuation thereof.

In yet another alternative embodiment the substance supply unit 149 could comprise a nebulizer which delivers metered doses of a substance, as an aerosol spray, on actuation thereof.

Operation of the delivery device will now be described hereinbelow with reference to FIGS. 10 to 13 of the accompanying drawings.

Figure 11:
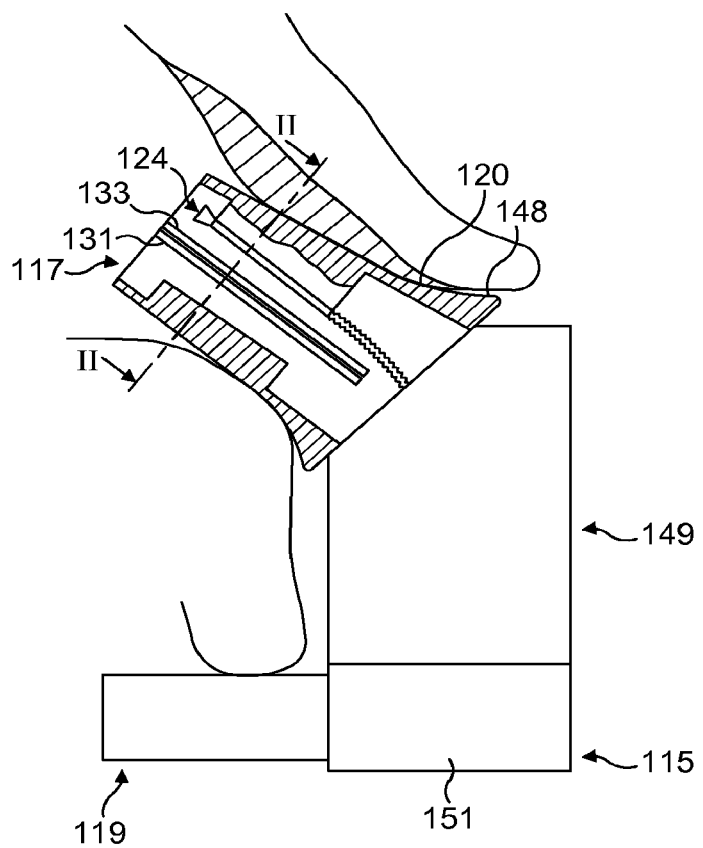
FIG. 11 illustrates the delivery device of FIG. 8 inserted into a nasal cavity of a subject prior to operation.

Referring to FIGS. 10 and 11, the nosepiece assembly 117 is first inserted into one of the nasal cavities of a subject until the sealing member 148 abuts the nares of the nostril of the subject, at which point the distal end of the outlet unit 124 typically extends from about 2 cm to about 4 cm into the nasal cavity of the subject, and the mouthpiece unit 119 is then gripped in the lips of the subject.

Figure 12:
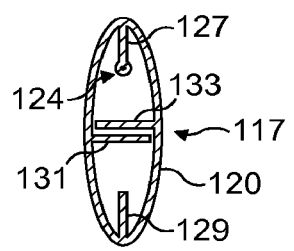
FIG. 12 illustrates a cross sectional view (along section II-II in FIG. 11) of the nosepiece assembly of the delivery device of FIG. 8 inserted into the nasal cavity of the subject for operation.

As illustrated in FIG. 12, insertion of the nosepiece 120 into the nasal cavity of the subject acts to compress the lateral sections of the nosepiece 120 by engagement with the relatively-narrow passage as presented at the nasal valve, which in turn acts to cause the expansion of the upper and lower sections of the nosepiece 120 in the vertical axis, with the extent of the compression being determined by the supporting elements 131, 133. This expansion acts to engage upper and lower walls of the nasal cavity of the subject and cause the expansion of the nasal cavity in the vertical plane, in particular the upper wall of the nasal cavity of the subject, which is a fleshy structure, as compared to the lower wall of the nasal cavity of the subject, which is a relatively-hard structure, and also position the nosepiece 120 in the nasal cavity of the subject, with the lower wall of the nasal cavity of the subject, in being a relatively-hard structure, acting as a reference for the expansion. This expansion further acts to tension the lateral walls of the nasal cavity of the subject which defines the nasal valve, which causes the lateral walls of the nasal cavity to be urged into sealing contact with the nosepiece 120.

Figure 13:
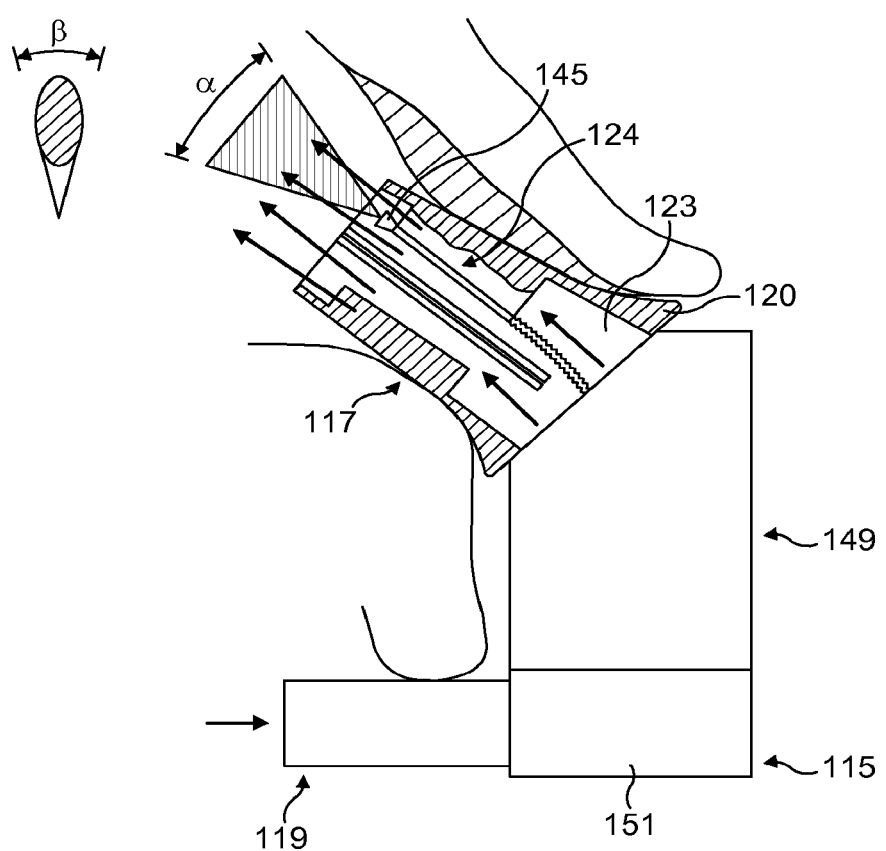
FIG. 13 illustrates the delivery device of FIG. 8 following actuation of the substance supply unit.
Figure 14:
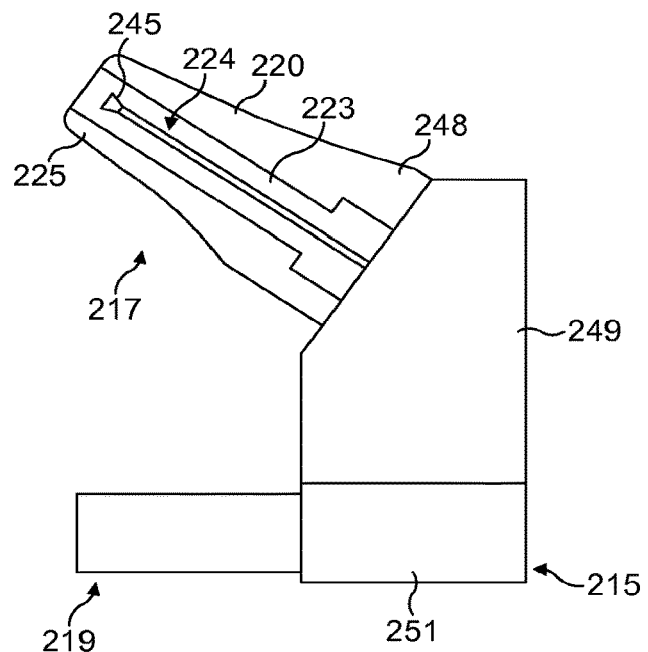
FIG. 14 illustrates a nasal delivery device in accordance with a third embodiment of the present invention.

Referring to FIG. 13, the subject then begins to exhale through the mouthpiece unit 119, which exhalation acts to close the oropharyngeal velum of the subject and drive an air flow through the delivery channel 123 of the nosepiece 120, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 123 of the nosepiece 120 reaches a predetermined value, the release mechanism 151 is triggered to actuate the substance supply unit 149 to deliver a metered dose of a substance to the nozzle 145 of the outlet unit 124 and into the nasal cavity of the subject, in this embodiment as an asymmetric aerosol spray. In the alternative embodiment the release mechanism 151 could be triggered on the generation of a predetermined pressure in the delivery channel 123 of the nosepiece 120.

Following exhalation, the subject then releases the mouthpiece unit 119 and the nosepiece assembly 117 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 149.

FIGS. 14 to 20 illustrate a nasal delivery device in accordance with a third embodiment of the present invention.

The delivery device comprises a housing 215, a nosepiece assembly 217 for fitting in a nasal cavity of a subject, and a mouthpiece unit 219 through which the subject exhales to actuate the delivery device.

The nosepiece assembly 217 comprises a nosepiece 220 which is attached to the housing 115 and defines a delivery channel 223 which is in fluid communication with the mouthpiece unit 219 such that an air flow is delivered into and through the nasal airway of the subject on exhalation by the subject through the mouthpiece unit 219, and an outlet unit 224 which is disposed within the nosepiece 220 for delivering substance into the nasal airway of the subject.

Figure 15:
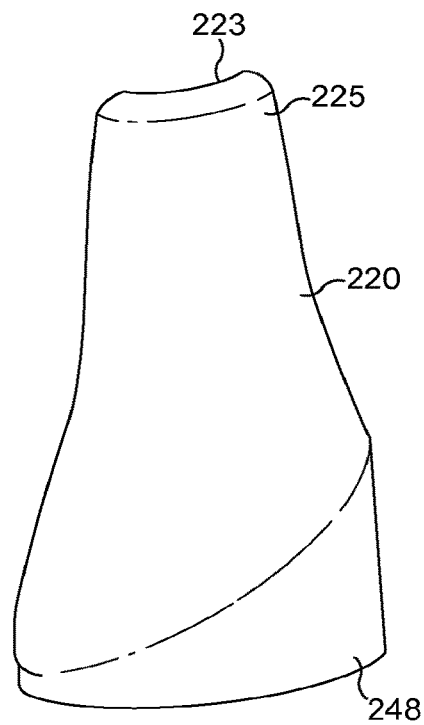
FIG. 15 illustrates a fragmentary perspective view of the nosepiece of the delivery device of FIG. 14 (other side symmetrical)
Figure 16:
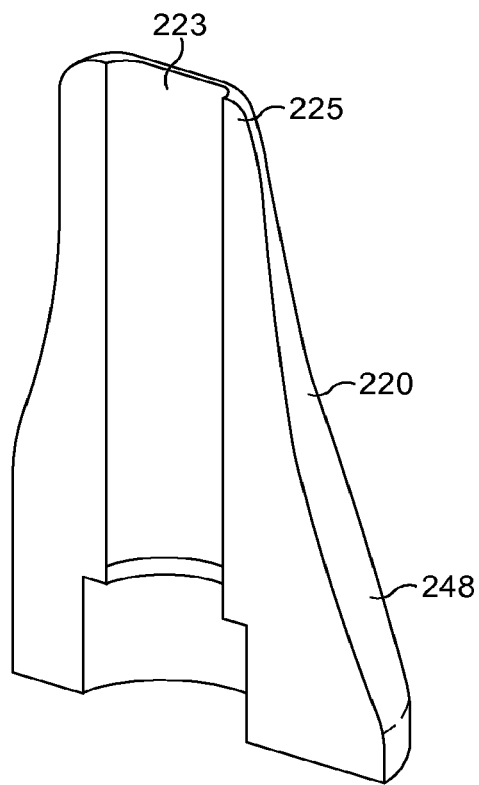
FIG. 16 illustrates a fragmentary, sectional perspective view of the nosepiece of the delivery device of FIG. 14 (other side symmetrical)
Figure 17:
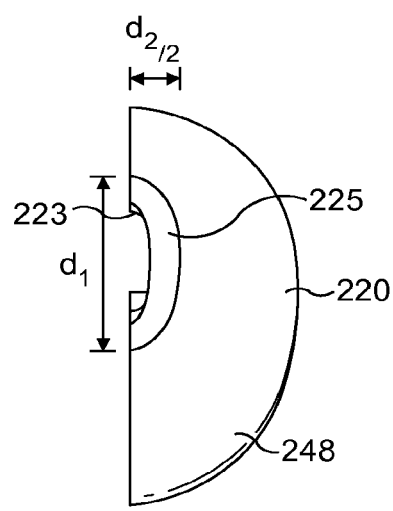
FIG. 17 illustrates a fragmentary plan view of the nosepiece of the delivery device of FIG. 14 (other side symmetrical)

In this embodiment, as particularly illustrated in FIGS. 15 to 17, the nosepiece 220 is generally frusto-conical in shape and includes a tip element 225 of asymmetric, elongate section, in having a dimension d1 in a first, sagittal direction which is substantially greater than a dimension d2 in a second, lateral direction which is orthogonal to the first, sagittal direction. In this embodiment the dimension d1 in the sagittal direction is at least twice that of the dimension d2 in the lateral direction. In one embodiment the dimension d2 in the lateral direction is not more than 6 mm and more preferably not more than 4 mm.

In this embodiment the tip element 225 extends substantially axially to the longitudinal axis of the nosepiece 220.

In this embodiment the nosepiece 220 further comprises a sealing element 248, in this embodiment a tapered, annular section, which acts both to provide a seal with the nares of the nostril of the nasal cavity of the subject and determine the extent of the insertion of the outlet unit 224 of the nosepiece assembly 217 into the nasal cavity of the subject. In a preferred embodiment the distal end of the outlet unit 224 is configured to extend at least about 2 cm, preferably at least about 3 cm, more preferably at least about 4 cm, and preferably from about 2 cm to about 4 cm, into the nasal cavity of the subject.

In this embodiment the nosepiece 220 is formed as a substantially rigid structure, here formed of a plastics material.

In this embodiment the outlet unit 224 comprises a nozzle 245 for delivering substance to the nasal airway of the subject.

In this embodiment the nozzle 245 is configured to provide an aerosol spray, either as a liquid or powder aerosol.

In an alternative embodiment the nozzle 245 could be configured to deliver a jet as a column of substance, either as a liquid or powder jet.

With this configuration, as will be described in more detail hereinbelow, on insertion of the nosepiece 220 into the nasal cavity of the subject, the longer, sagittal section of the tip element 225 of the nosepiece 220 becomes aligned in the sagittal plane and acts to engage upper and lower walls of the nasal cavity of the subject and cause the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 220 in the nasal cavity of the subject, with the lower wall of the nasal cavity of the subject, in being a relatively-hard structure, acting as a reference for the expansion.

This expansion further acts to tension the lateral walls of the nasal cavity of the subject which defines the nasal valve, which causes the lateral walls of the nasal cavity to be urged into sealing contact with the nosepiece 220.

In this embodiment the nozzle 245 of the outlet unit 224 is configured to deliver an asymmetric aerosol spray, with the aerosol spray having a significantly greater spray angle in the vertical, sagittal plane α than in the horizontal plane β. Such an aerosol spray has been found to be particularly advantageous in the delivery of substance to posterior regions of the nasal cavities, in particular the olfactory region.

In a preferred embodiment the spray angle in the vertical, sagittal plane α is greater than about 35°, more preferably greater than about 40°, still more preferably greater than about 45° and yet more preferably greater than about 50°.

In a preferred embodiment the spray angle in the horizontal plane β is not more than about 35°, more preferably not more than about 30°, still more preferably not more than about 25°, yet more preferably not more than about 20°, and still yet more preferably not more than about 15°.

In this embodiment the aerosol spray presents an elliptical spray zone.

In another embodiment the aerosol spray could present a substantially rectangular spray zone.

The delivery device further comprises a substance supply unit 249 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 245 of the outlet unit 224 to deliver substance from the nosepiece assembly 217, in this embodiment as an aerosol spray.

In this embodiment the substance supply unit 249 is a multi-dose unit for delivering a plurality of metered doses of substance. In another embodiment the substance supply unit 249 could be a single-dose unit for delivering a single metered dose of substance.

The substance supply unit 249 is pre-primeable, in this embodiment by loading a resilient element, and includes a breath-actuated release mechanism 251 which, when triggered, releases the resilient element and actuates the substance supply unit 249 to deliver a metered dose of substance through the nozzle 245 of the outlet unit 224.

In this embodiment the release mechanism 251 is configured to cause actuation of the substance supply unit 249 on generation of a predetermined flow rate through the delivery channel 223 of the nosepiece 220.

In another embodiment the release mechanism 251 could be configured to cause actuation of the substance supply unit 249 on generation of a predetermined pressure within the delivery channel 223 of the nosepiece 220.

In a further embodiment the release mechanism 251 could be configured to cause actuation of the substance supply unit 249 on generation of either one of a predetermined flow rate through the delivery channel 223 of the nosepiece 220 or a predetermined pressure within the delivery channel 223 of the nosepiece 220.

In an alternative embodiment the substance supply unit 249 could comprise a mechanical delivery pump, in particular a liquid delivery pump or a powder delivery pump, which delivers metered doses of a substance on actuation thereof.

In another alternative embodiment the substance supply unit 249 could comprise a dry powder delivery unit which delivers metered doses of a substance, as a dry powder, on actuation thereof.

In yet another alternative embodiment the substance supply unit 249 could comprise a nebulizer which delivers metered doses of a substance, as an aerosol spray, on actuation thereof.

Operation of the delivery device will now be described hereinbelow with reference to FIGS. 18 to 20 of the accompanying drawings.

Figure 18:
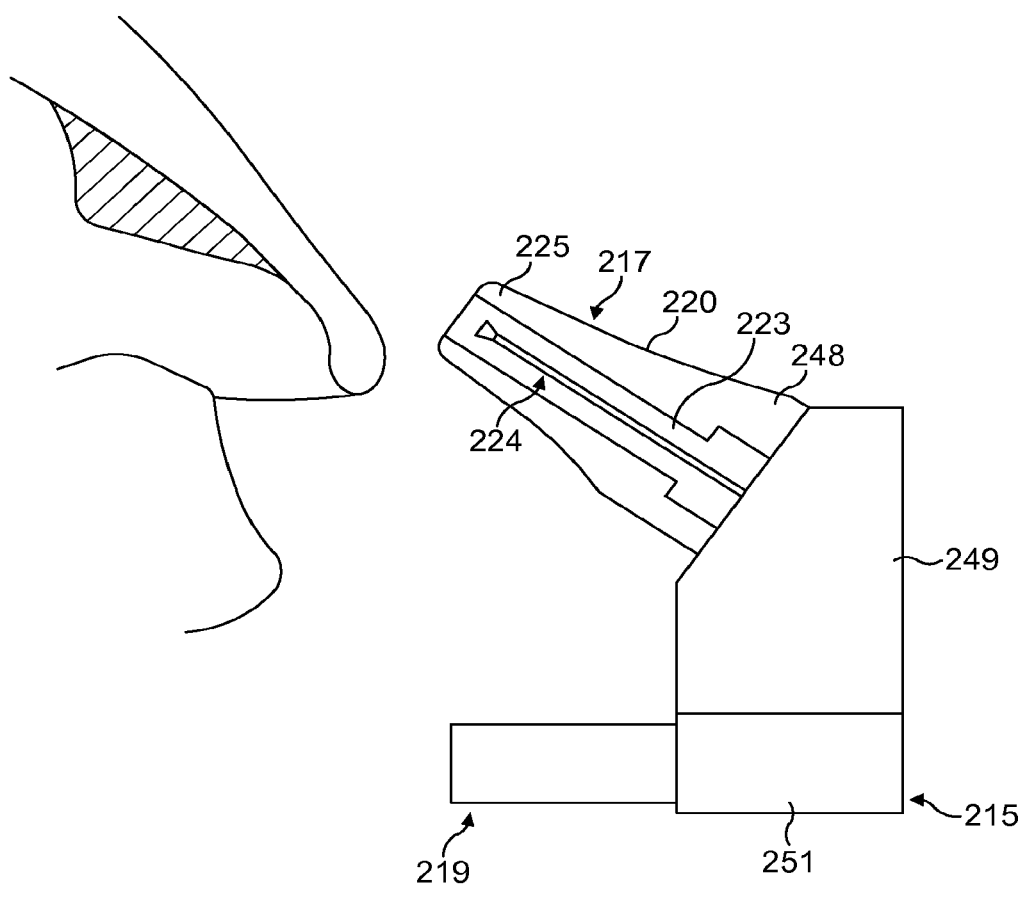
FIG. 18 illustrates the delivery device of FIG. 14 prior to insertion into a nasal cavity of a subject.
Figure 19:
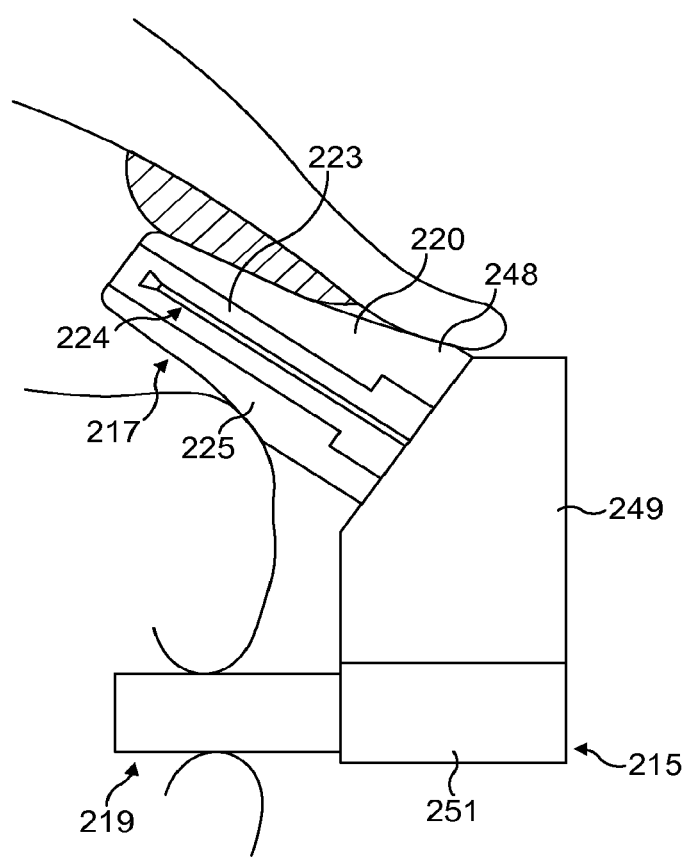
FIG. 19 illustrates the delivery device of FIG. 14 inserted into a nasal cavity of the subject prior to operation.

Referring to FIGS. 18 and 19, the nosepiece assembly 217 is first inserted into one of the nasal cavities of a subject until the sealing member 248 abuts the nares of the nostril of the subject, at which point the distal end of the outlet unit 224 typically extends from about 2 cm to about 4 cm into the nasal cavity of the subject, and the mouthpiece unit 219 is then gripped in the lips of the subject.

As illustrated, insertion of the nosepiece 220 into the nasal cavity of the subject acts to cause the longer, sagittal section of the tip element 225 of the nosepiece 220 to become aligned in the sagittal plane and engage upper and lower walls of the nasal cavity of the subject, which engagement causes the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 220 in the nasal cavity of the subject, with the lower wall of the nasal cavity of the subject, in being a relatively-hard structure, acting as a reference for the expansion. This expansion further acts to tension the lateral walls of the nasal cavity of the subject which defines the nasal valve, which causes the lateral walls of the nasal cavity to be urged into sealing contact with the nosepiece 220.

Figure 20:
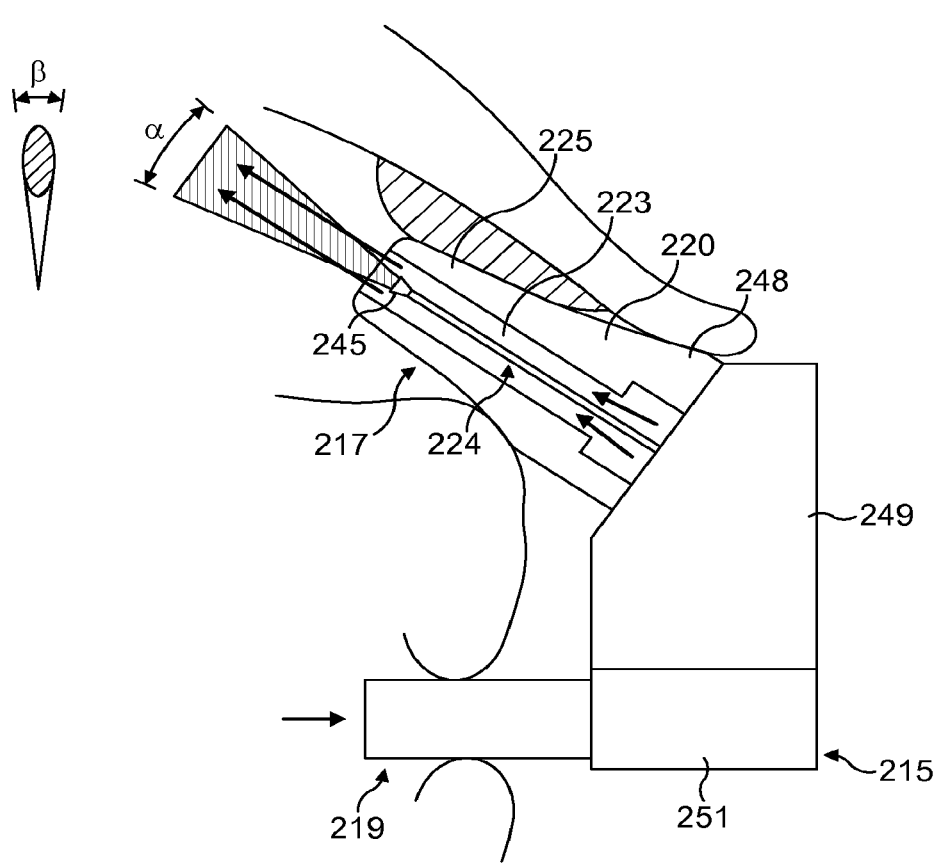
FIG. 20 illustrates the delivery device of FIG. 14 following actuation of the substance supply unit.
Figure 21:
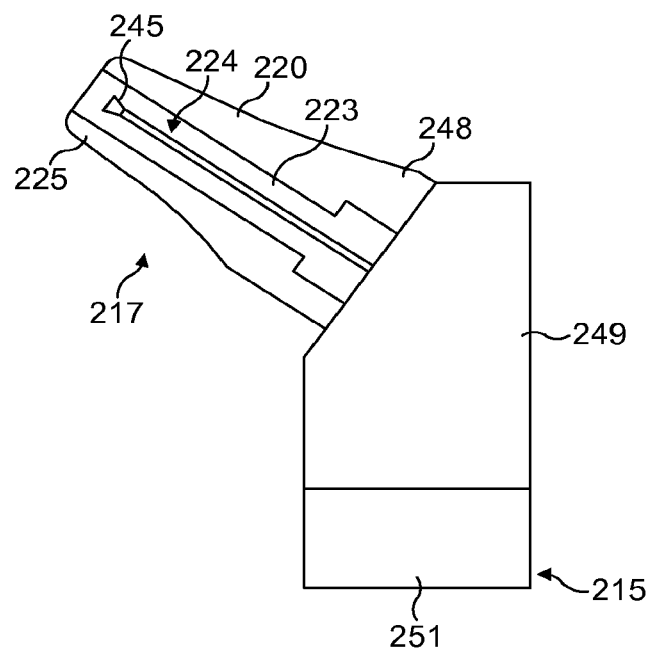
FIG. 21 illustrates a nasal delivery device in accordance with a fourth embodiment of the present invention.
Figure 22:
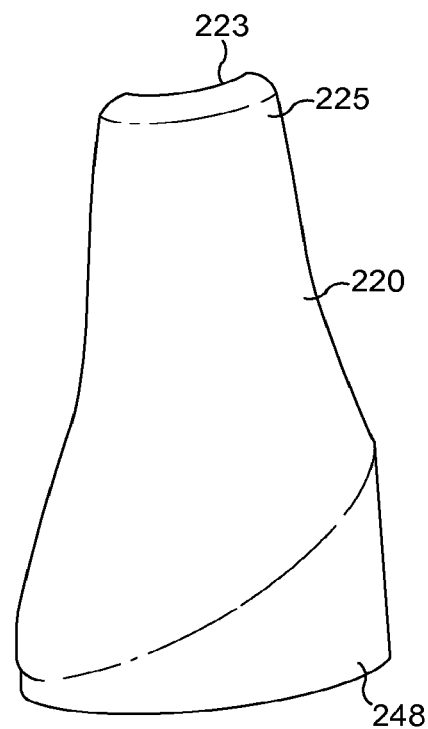
FIG. 22 illustrates a fragmentary perspective view of the nosepiece of the delivery device of FIG. 21 (other side symmetrical)
Figure 23:
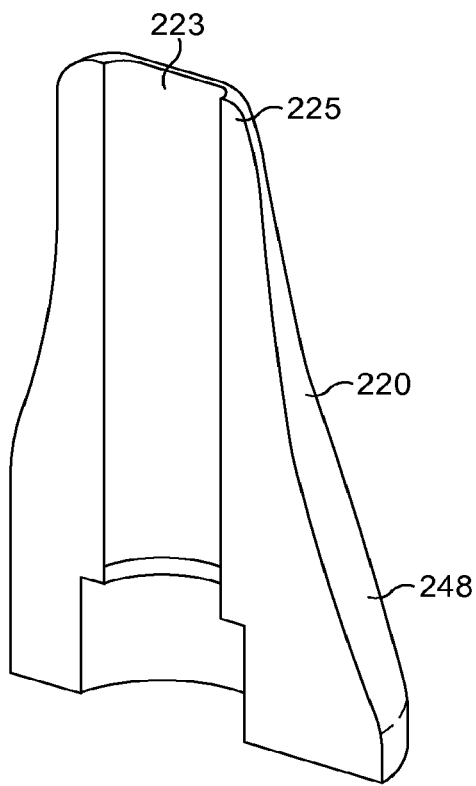
FIG. 23 illustrates a fragmentary, sectional perspective view of the nosepiece of the delivery device of FIG. 21 (other side symmetrical)
Figure 24:
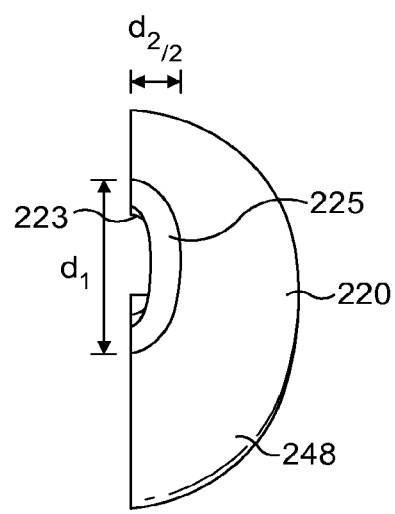
FIG. 24 illustrates a fragmentary plan view of the nosepiece of the delivery device of FIG. 21 (other side symmetrical)
Figure 25:
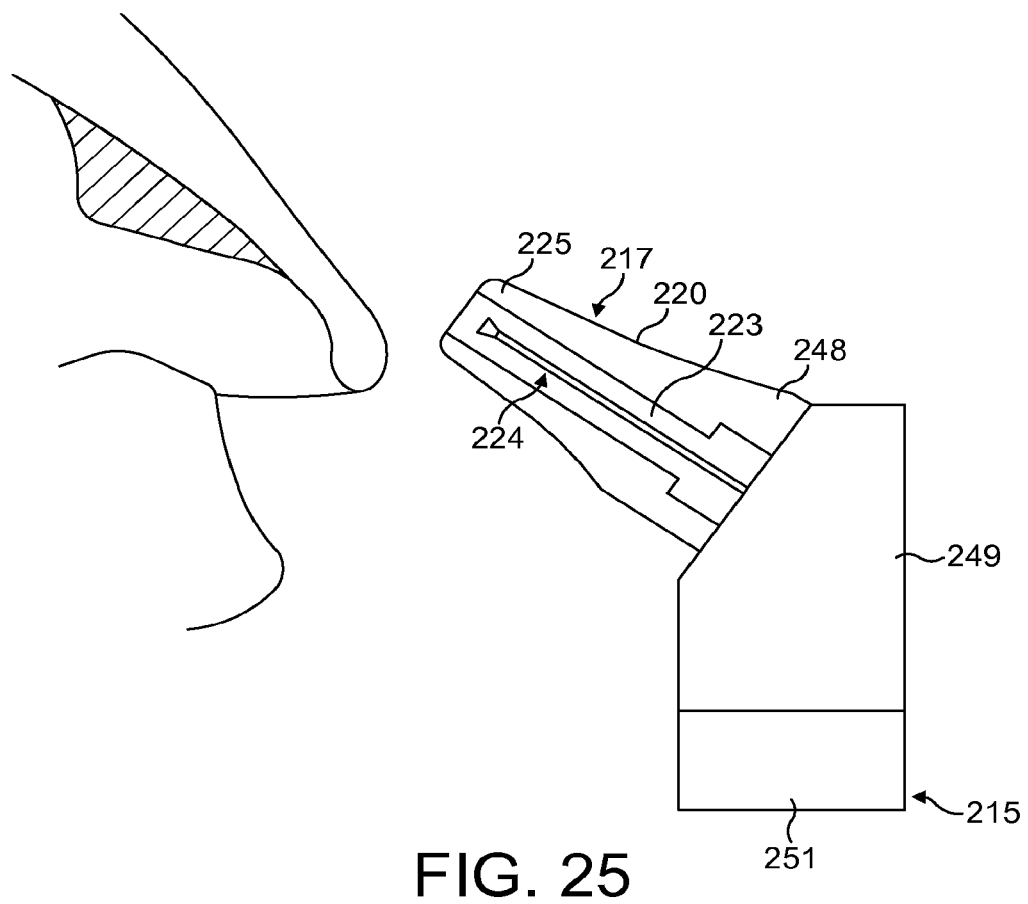
FIG. 25 illustrates the delivery device of FIG. 21 prior to insertion into a nasal cavity of a subject.
Figure 26:
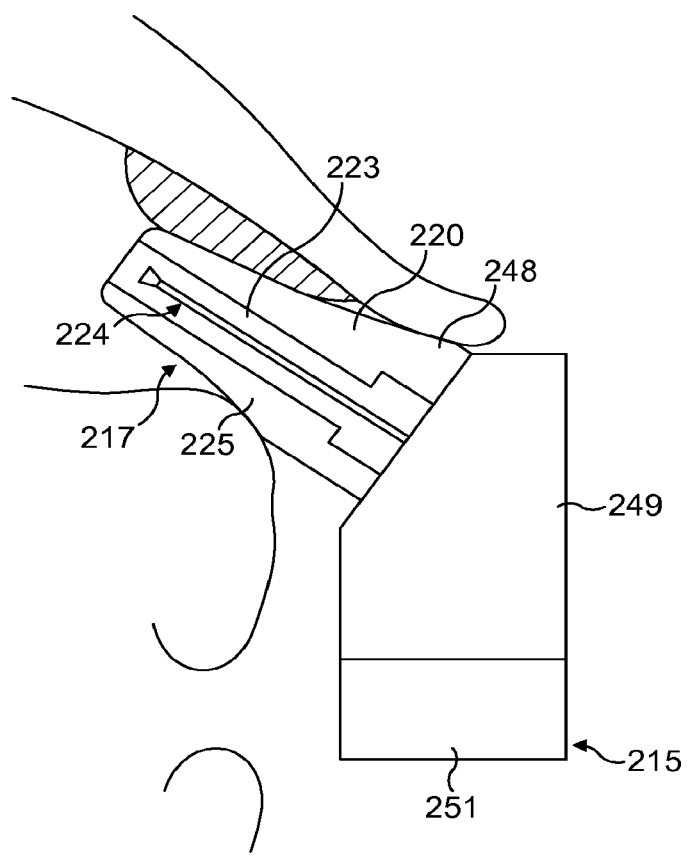
FIG. 26 illustrates the delivery device of FIG. 21 inserted into a nasal cavity of the subject prior to operation.
Figure 27:
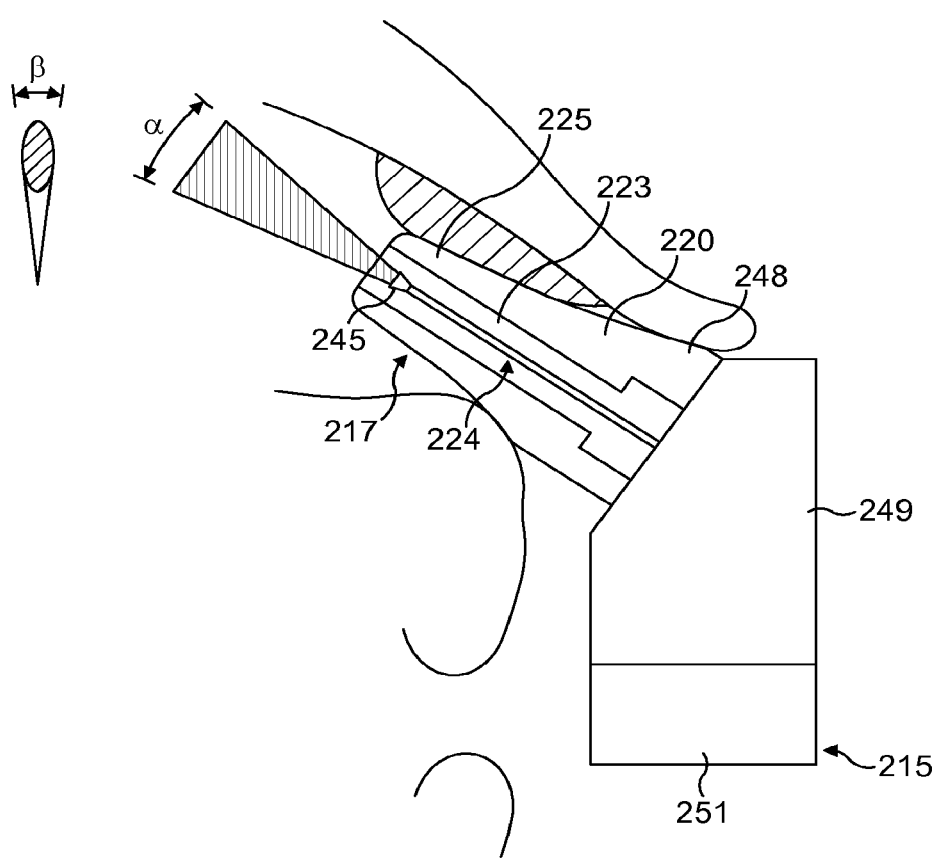
FIG. 27 illustrates the delivery device of FIG. 21 following actuation of the substance supply unit.
Figure 28:
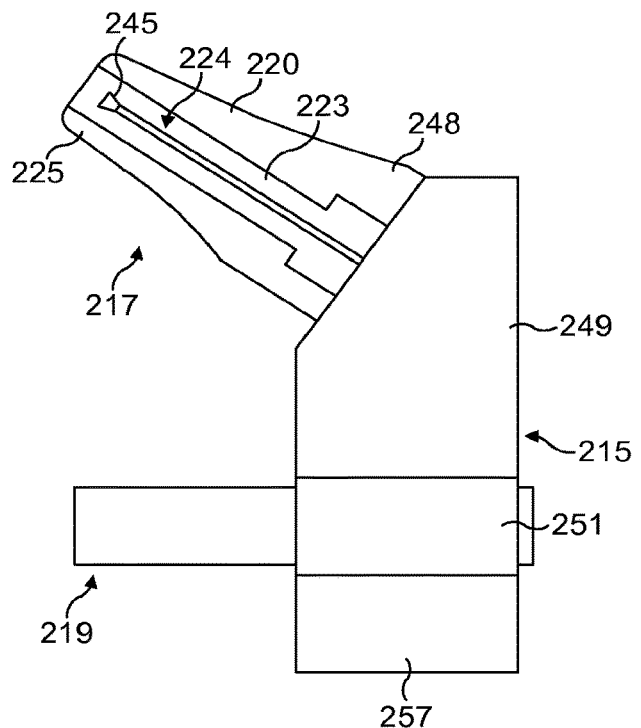
FIG. 28 illustrates a nasal delivery device in accordance with a fifth embodiment of the present invention.
Figure 29:
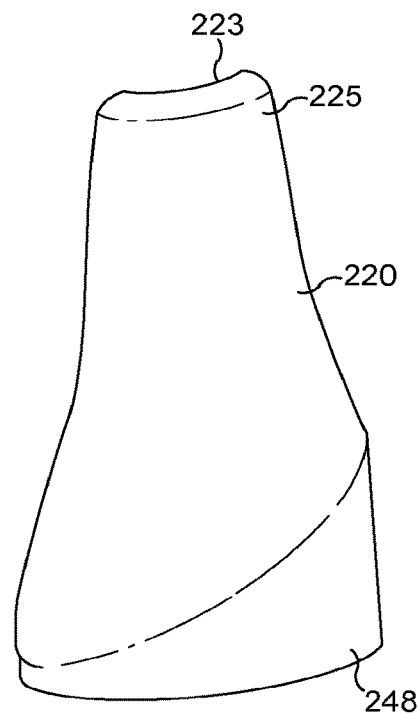
FIG. 29 illustrates a fragmentary perspective view of the nosepiece of the delivery device of FIG. 28 (other side symmetrical)
Figure 30:
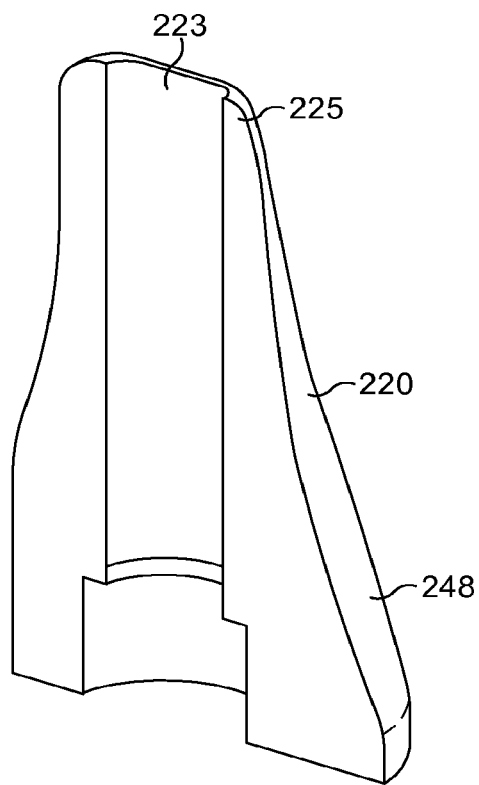
FIG. 30 illustrates a fragmentary, sectional perspective view of the nosepiece of the delivery device of FIG. 28 (other side symmetrical)
Figure 31:
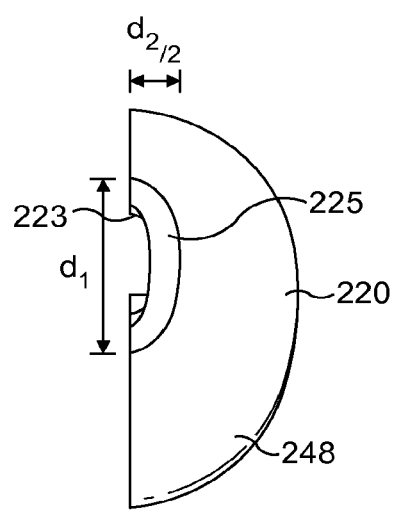
FIG. 31 illustrates a fragmentary plan view of the nosepiece of the delivery device of FIG. 28 (other side symmetrical)
Figure 32:
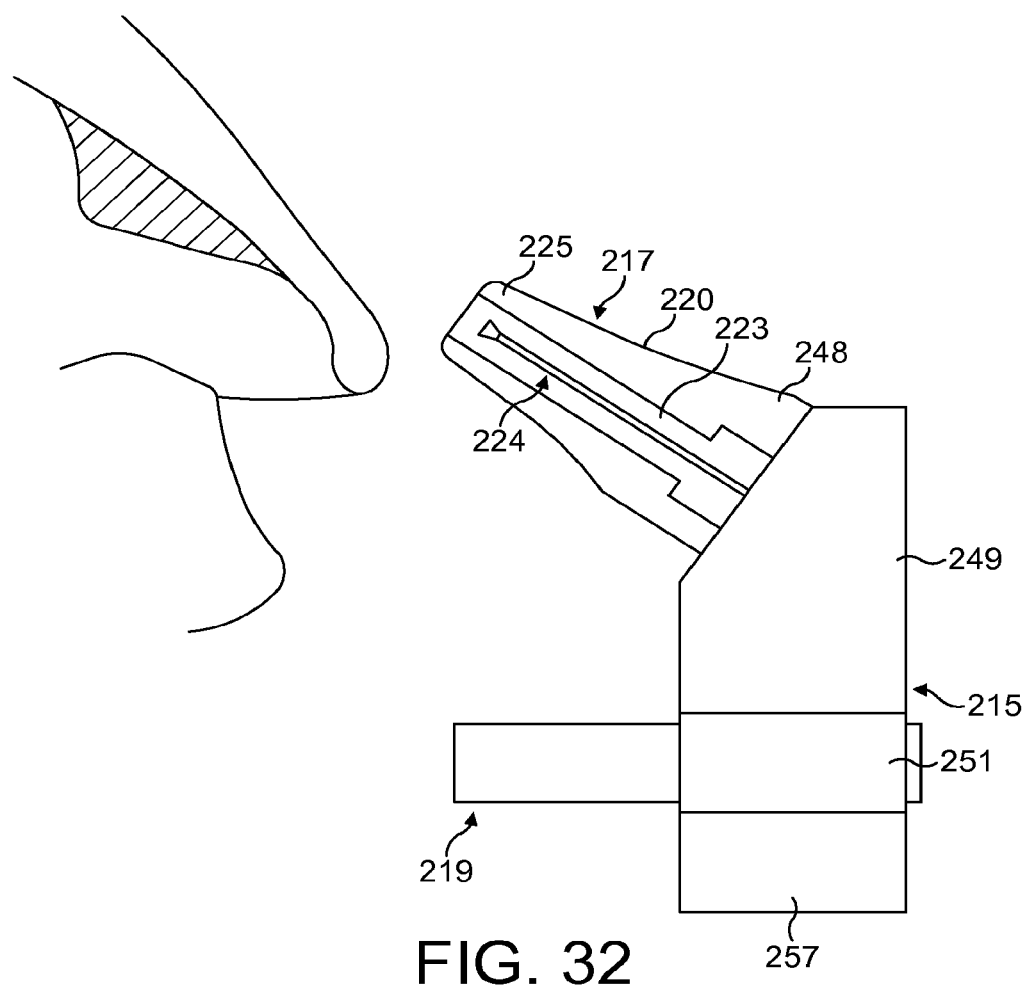
FIG. 32 illustrates the delivery device of FIG. 28 prior to insertion into a nasal cavity of a subject.
Figure 33:
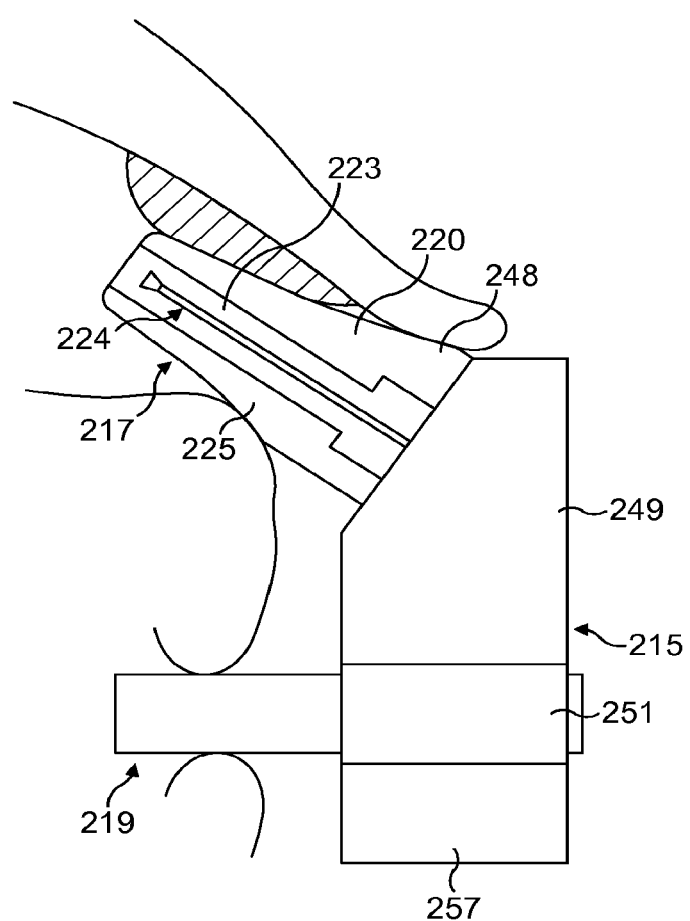
FIG. 33 illustrates the delivery device of FIG. 28 inserted into a nasal cavity of the subject prior to operation.
Figure 34:
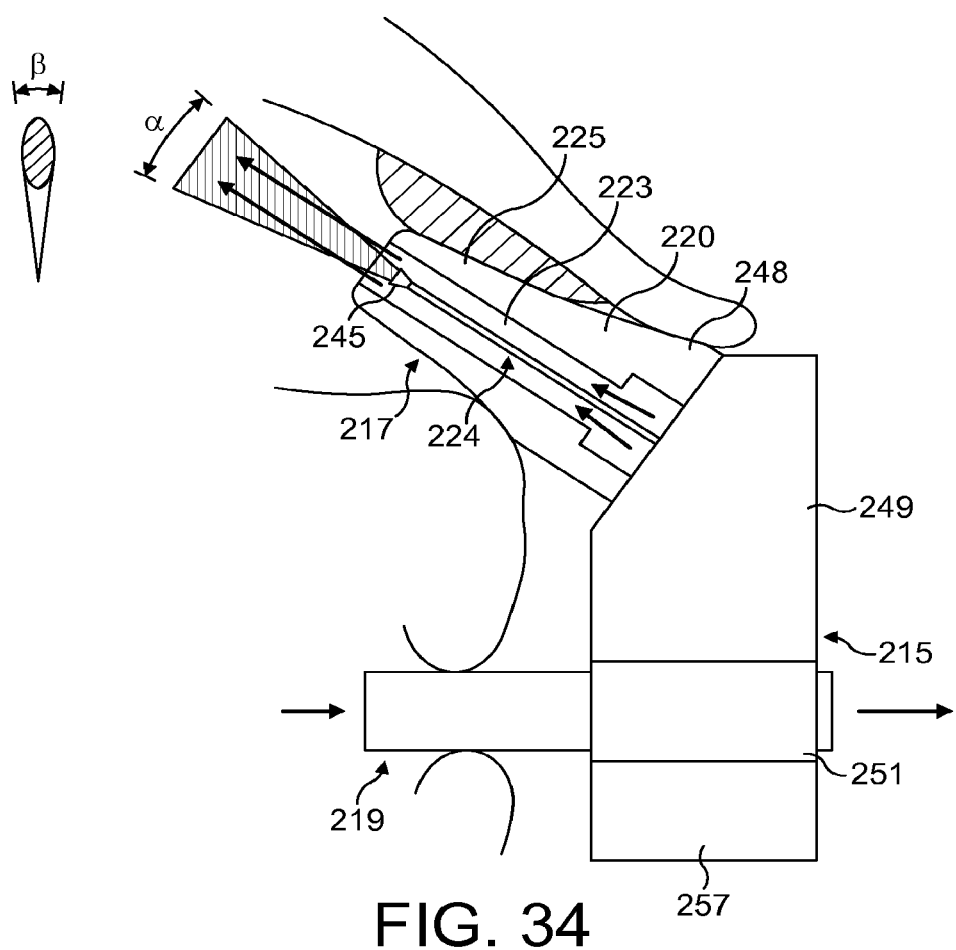
FIG. 34 illustrates the delivery device of FIG. 28 following actuation of the substance supply unit.
Figure 35:
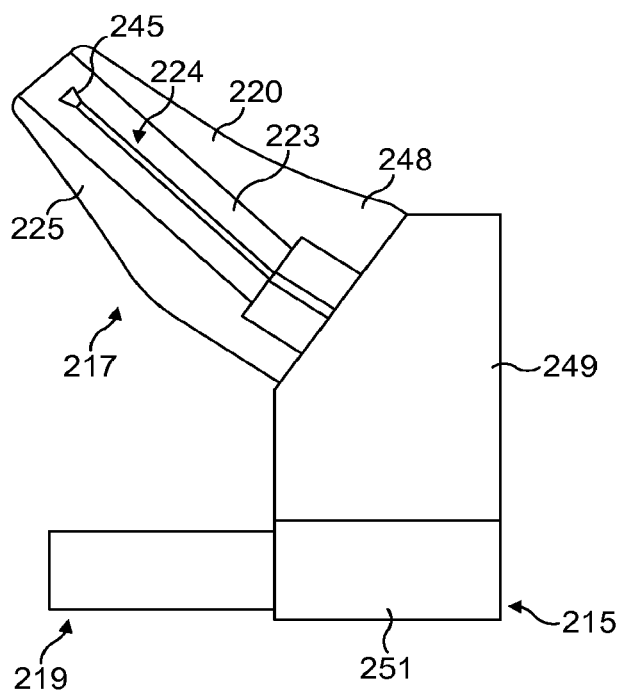
FIG. 35 illustrates a nasal delivery device in accordance with a sixth embodiment of the present invention.
Figure 36:
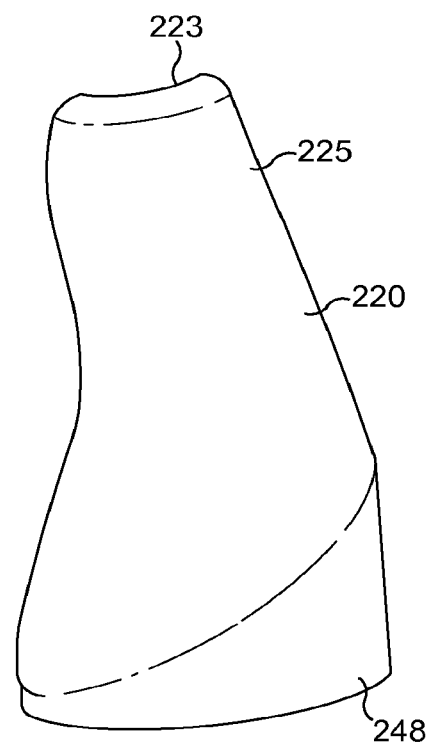
FIG. 36 illustrates a fragmentary perspective view of the nosepiece of the delivery device of FIG. 35 (other side symmetrical)
Figure 37:
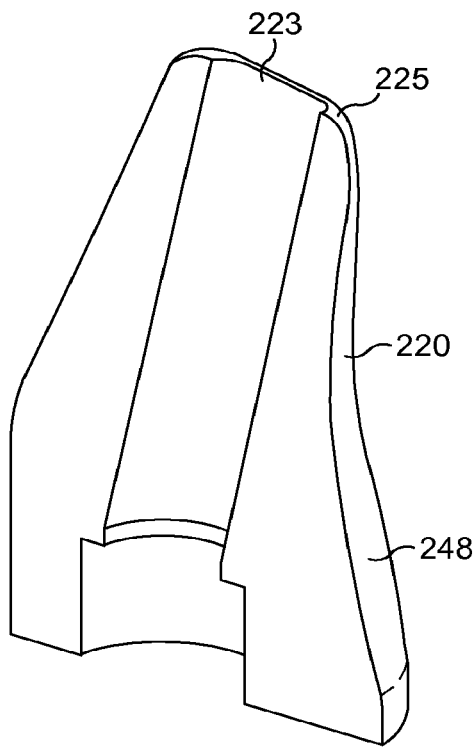
FIG. 37 illustrates a fragmentary, sectional perspective view of the nosepiece of the delivery device of FIG. 35 (other side symmetrical)
Figure 38:
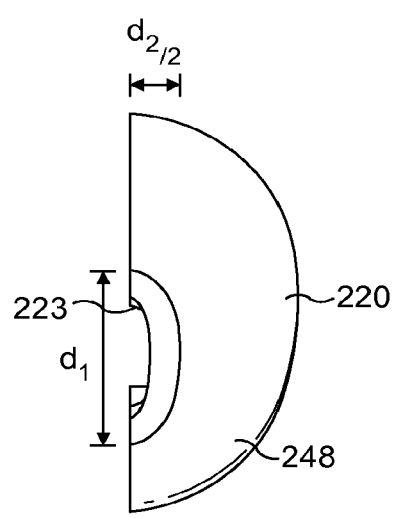
FIG. 38 illustrates a fragmentary plan view of the nosepiece of the delivery device of FIG. 35 (other side symmetrical)
Figure 39:
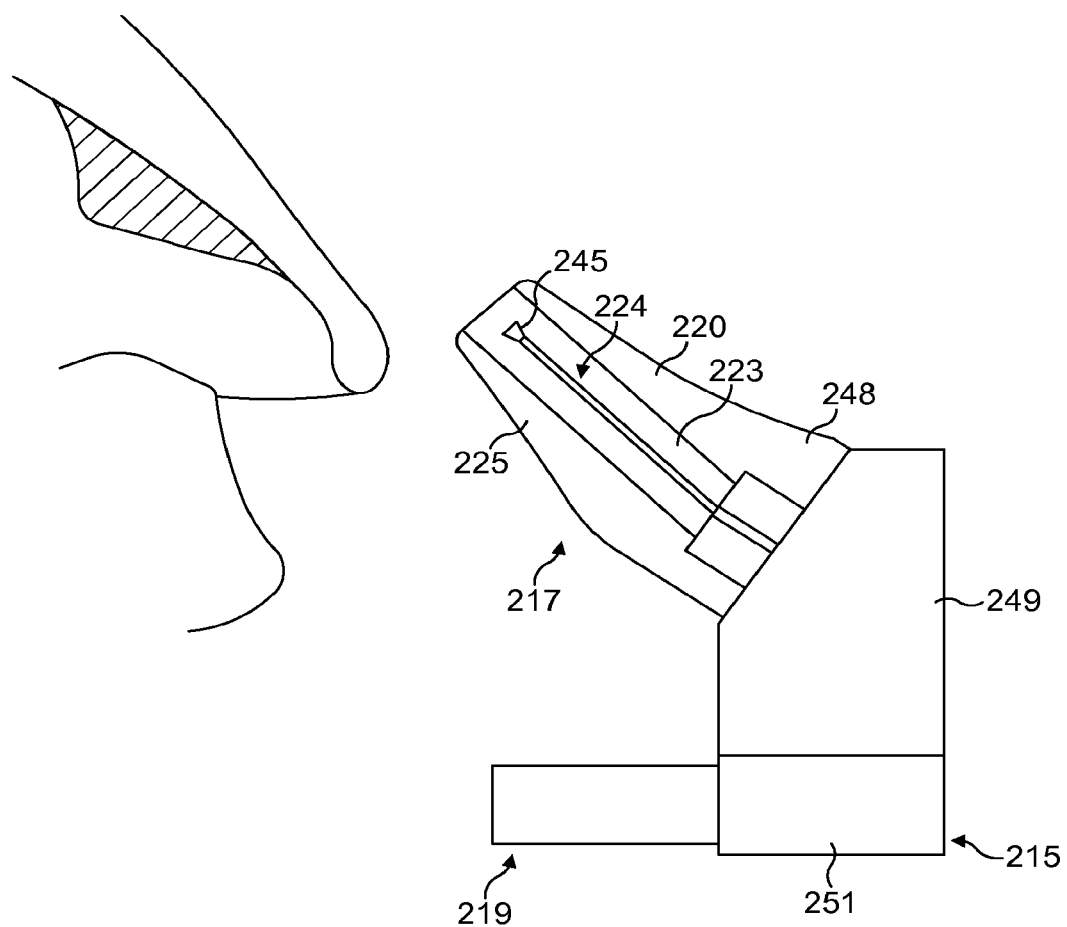
FIG. 39 illustrates the delivery device of FIG. 35 prior to insertion into a nasal cavity of a subject.

Referring to FIG. 20, the subject then begins to exhale through the mouthpiece unit 219, which exhalation acts to close the oropharyngeal velum of the subject and drive an air flow through the delivery channel 223 of the nosepiece 220, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 223 of the nosepiece 220 reaches a predetermined value, the release mechanism 251 is triggered to actuate the substance supply unit 249 to deliver a metered dose of a substance to the nozzle 245 of the outlet unit 224 and into the nasal cavity of the subject, in this embodiment as an asymmetric aerosol spray. In an alternative embodiment the release mechanism 251 could be triggered on the generation of a predetermined pressure in the delivery channel 223 of the nosepiece 220.

Following exhalation, the subject then releases the mouthpiece unit 219 and the nosepiece assembly 217 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 249.

FIGS. 21 to 27 illustrate a nasal delivery device in accordance with a fourth embodiment of the present invention.

The delivery device of this embodiment is quite similar to the delivery device of the above-described third embodiment, and thus, in order to avoid unnecessary duplication of description, only the differences will be described in detail, with like reference signs designating like parts.

The delivery device of this embodiment differs from that of the above-described third embodiment in the release mechanism 251 being a manually-actuated unit and the mouthpiece unit 219 being omitted. With this configuration, a gas flow is not delivered into the nasal cavity of the subject, but the device still advantageously provides for delivery to the olfactory region by virtue of the operation of the nosepiece 220 of the nosepiece unit 217.

Operation of the delivery device is the same as for the above-described third embodiment, except that a gas flow is not delivered into the nasal cavity.

FIGS. 28 to 34 illustrate a nasal delivery device in accordance with a fifth embodiment of the present invention.

The delivery device of this embodiment is very similar to the delivery device of the above-described third embodiment, and thus, in order to avoid unnecessary duplication of description, only the differences will be described in detail, with like reference signs designating like parts.

The delivery device of this embodiment differs from that of the above-described third embodiment in further comprising an oral exhalation breath-actuatable gas supply unit 257 for delivering a gas flow through the delivery channel 223 of the outlet unit 221 in response to exhalation by a subject, and in that the mouthpiece unit 219 is not in fluid communication with the delivery channel 223 of the outlet unit 221, whereby a gas flow, separate to the exhalation breath of the subject, is delivered to the delivery channel 223 of the outlet unit 221, and hence the nasal airway of the subject, in response to exhalation through the mouthpiece unit 219.

Operation of the delivery device is the same as for the above-described third embodiment, with a gas flow, separate to the exhalation breath of the subject, being delivered to the delivery channel 223 of the outlet unit 221 in response to exhalation through the mouthpiece unit 219.

In one alternative embodiment the release mechanism 251 could be a manually-actuated unit and the mouthpiece unit 219 omitted.

FIGS. 35 to 41 illustrate a nasal delivery device in accordance with a sixth embodiment of the present invention.

The delivery device of this embodiment is very similar to the delivery device of the above-described third embodiment, and thus, in order to avoid unnecessary duplication of description, only the differences will be described in detail, with like reference signs designating like parts.

The delivery device of this embodiment differs from that of the above-described third embodiment in the configuration of the nosepiece 220 of the nosepiece unit 217.

Figure 40:
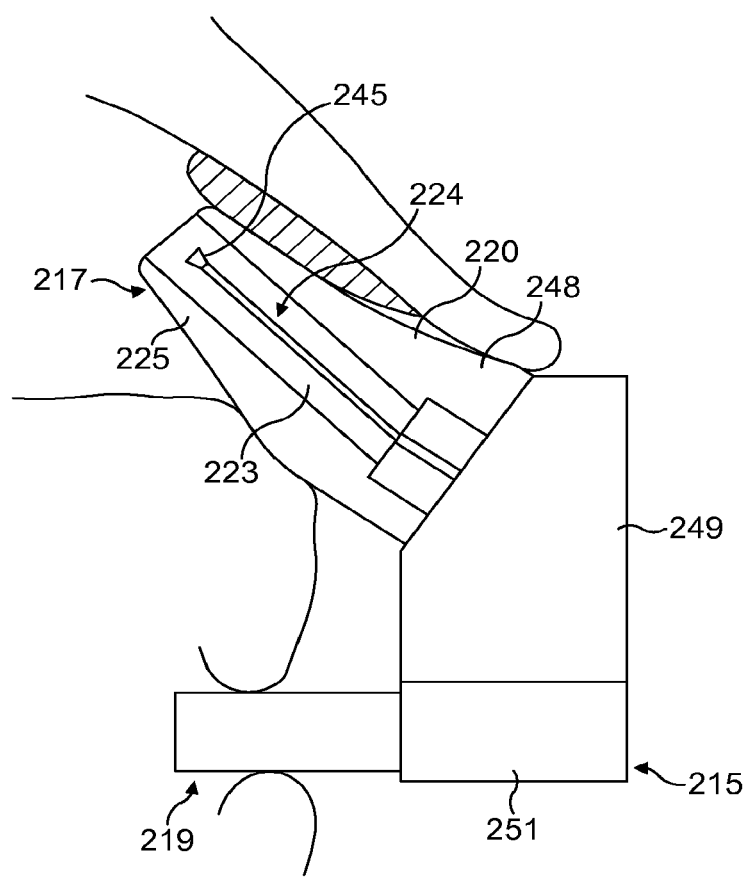
FIG. 40 illustrates the delivery device of FIG. 35 inserted into a nasal cavity of the subject prior to operation.
Figure 41:
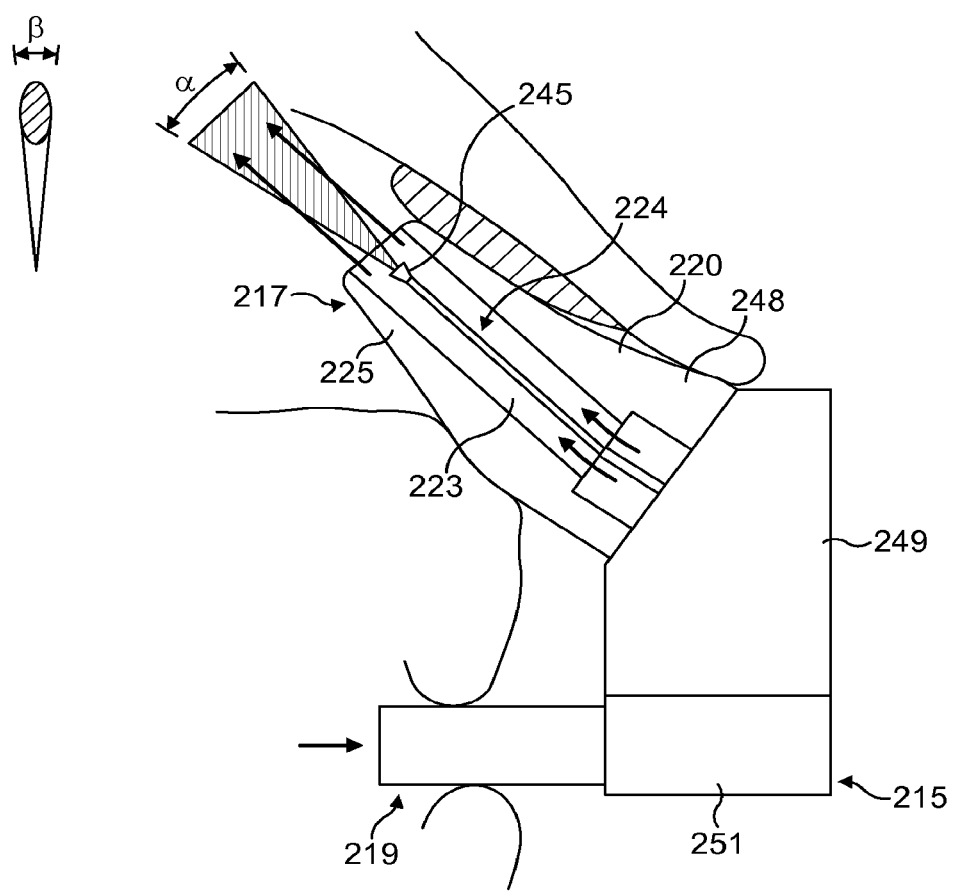
FIG. 41 illustrates the delivery device of FIG. 35 following actuation of the substance supply unit.
Figure 42:
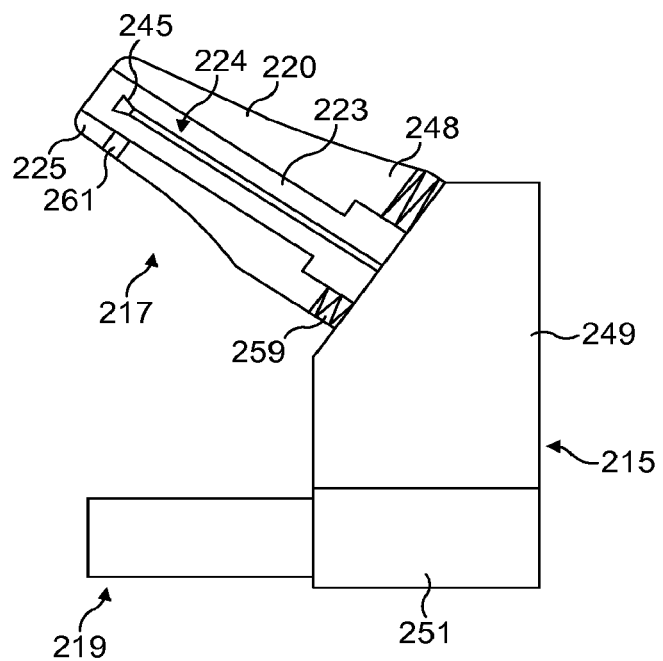
FIG. 42 illustrates a nasal delivery device in accordance with a seventh embodiment of the present invention.
Figure 43:
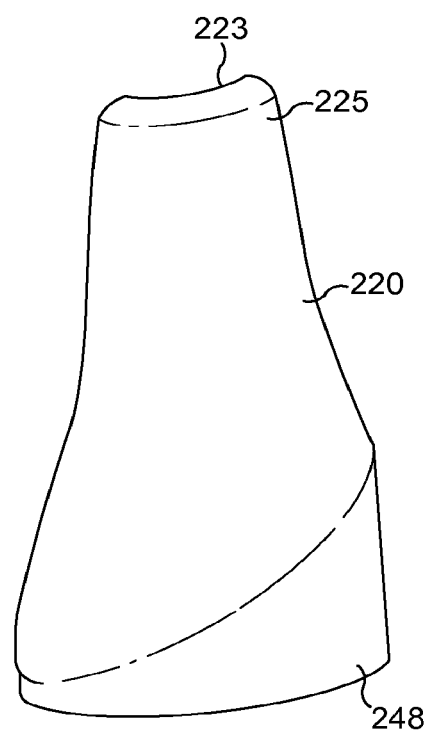
FIG. 43 illustrates a fragmentary perspective view of the nosepiece of the delivery device of FIG. 42 (other side symmetrical)
Figure 44:
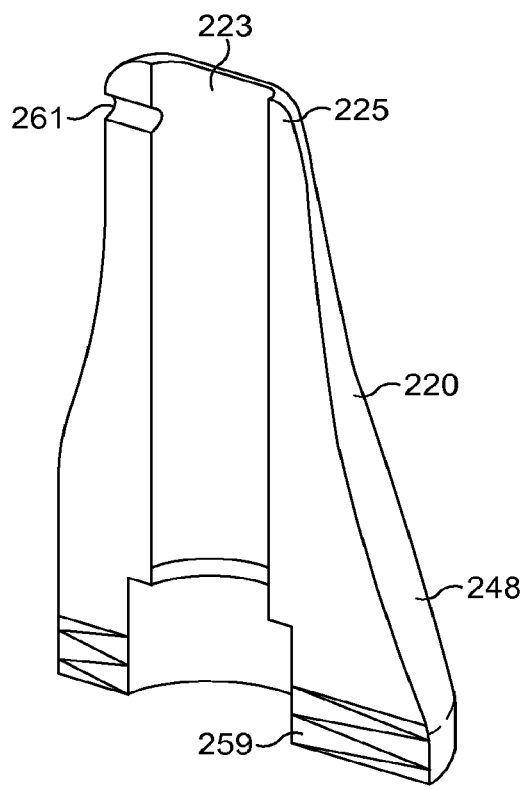
FIG. 44 illustrates a fragmentary, sectional perspective view of the nosepiece of the delivery device of FIG. 42 (other side symmetrical)
Figure 45:
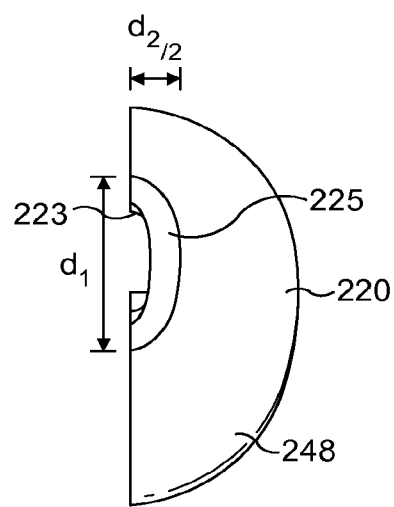
FIG. 45 illustrates a fragmentary plan view of the nosepiece of the delivery device of FIG. 42 (other side symmetrical)
Figure 46:
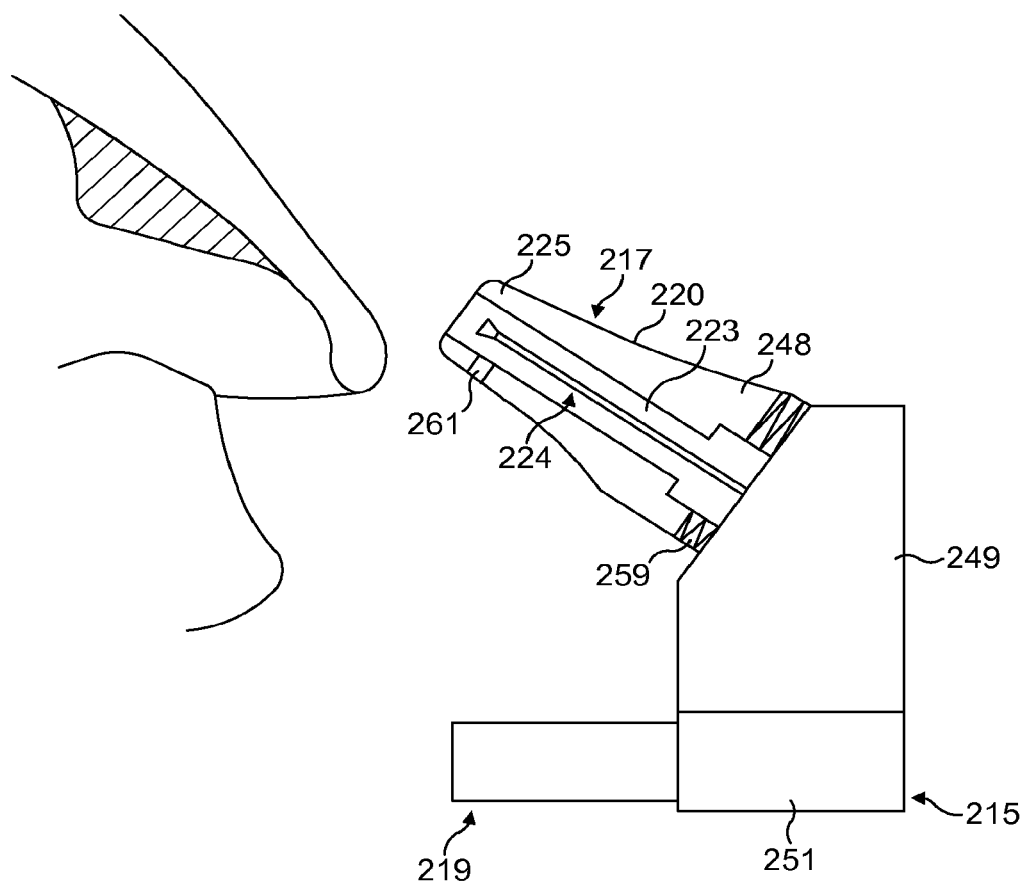
FIG. 46 illustrates the delivery device of FIG. 42 prior to insertion into a nasal cavity of a subject.
Figure 47:
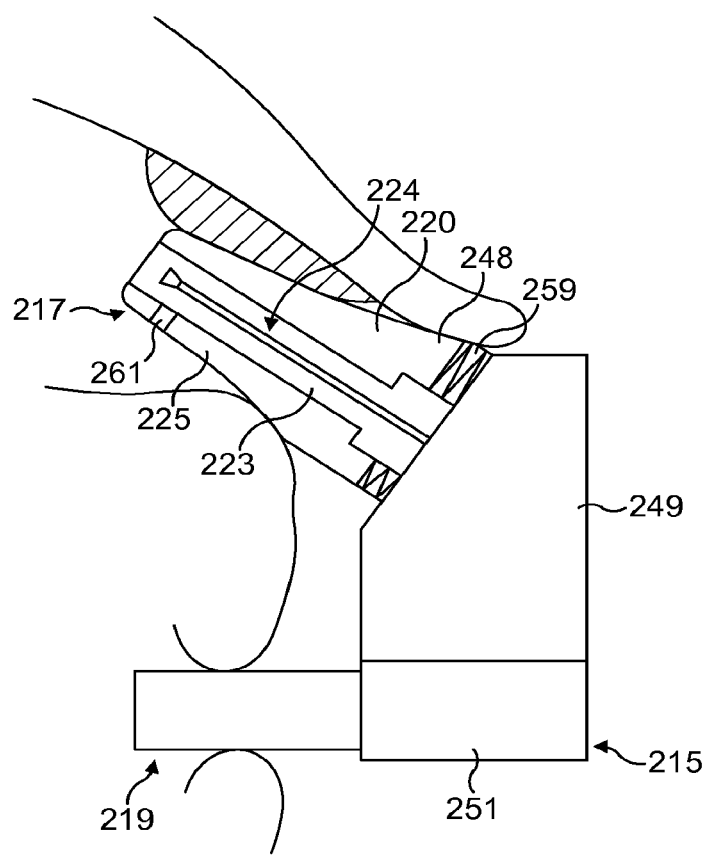
FIG. 47 illustrates the delivery device of FIG. 42 inserted into a nasal cavity of the subject prior to operation.
Figure 48:
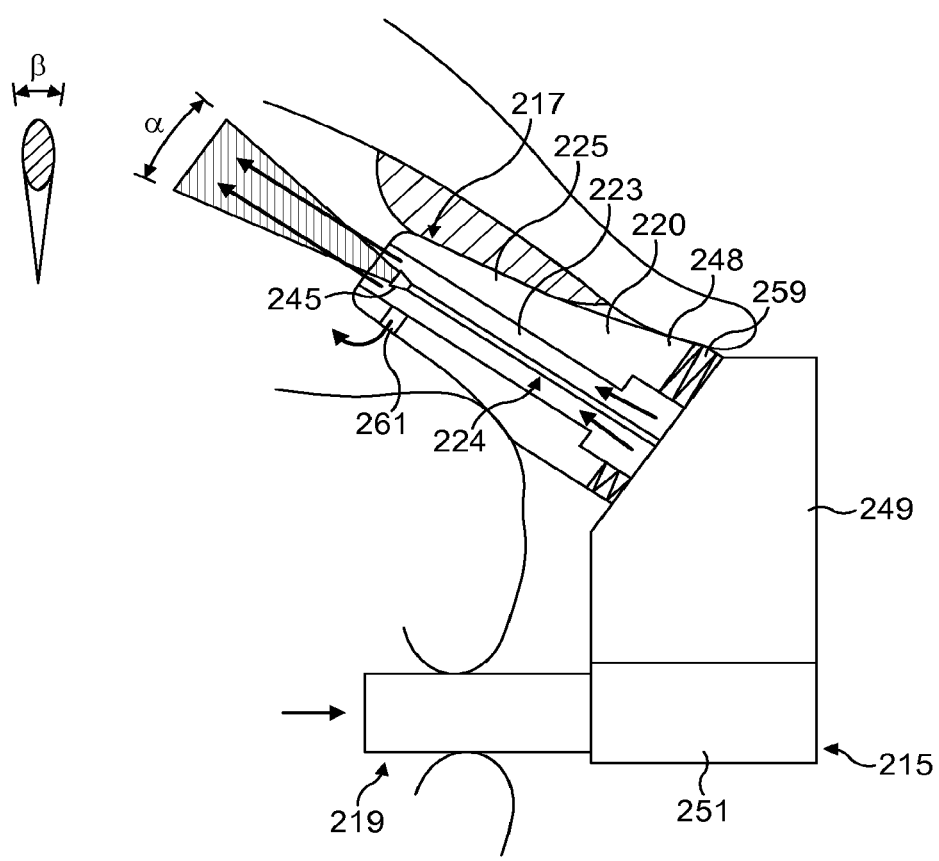
FIG. 48 illustrates the delivery device of FIG. 42 following actuation of the substance supply unit.
Figure 49:
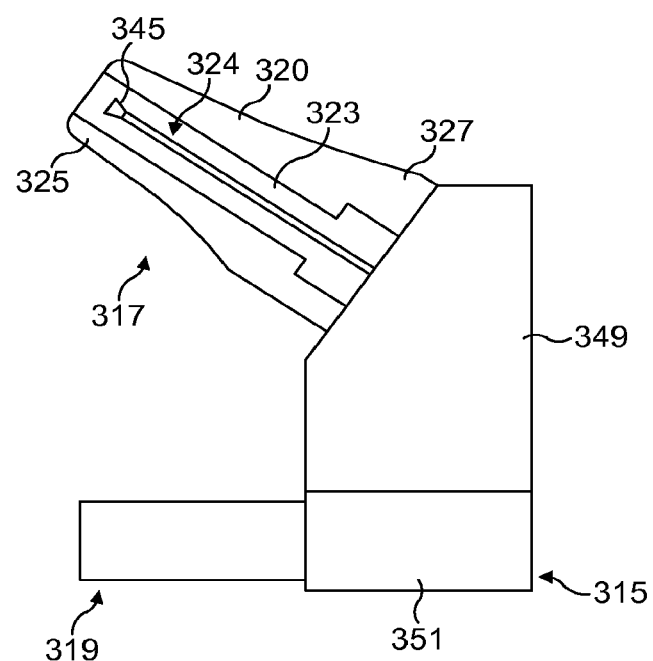
FIG. 49 illustrates a nasal delivery device in accordance with an eighth embodiment of the present invention.

In this embodiment the tip element 225 of the nosepiece 220 is inclined, in this embodiment upwardly, in the vertical, sagittal plane relative to the longitudinal axis of the nosepiece 220. As illustrated in FIGS. 40 and 41, this configuration is such as to provide for greater deflection of the upper surface of the nasal cavity relative to the bony and substantially rigid structure at the lower surface of the nasal cavity. With this configuration, the tip element 225 of the nosepiece 220 is inserted generally more caudally into the nasal opening, and subsequently rotated to the correct position by rotation.

Operation of the delivery device is the same as for the above-described third embodiment.

FIGS. 42 to 48 illustrate a nasal delivery device in accordance with a seventh embodiment of the present invention.

The delivery device of this embodiment is very similar to the delivery device of the above-described third embodiment, and thus, in order to avoid unnecessary duplication of description, only the differences will be described in detail, with like reference signs designating like parts.

The delivery device of this embodiment differs from that of the above-described third embodiment in the configuration of the nosepiece 220 of the nosepiece unit 217.

In this embodiment the nosepiece 220 is attached to the housing 215 by a flexible coupling 259, in this embodiment a resilient coupling, which allows for limited movement of the nosepiece 220 relative to the housing 215, which facilitates the fitting of the nosepiece 220 in a nasal cavity of the subject.

Also, in this embodiment the nosepiece 220 includes a lateral gas flow outlet 261, which is in fluid communication with the delivery channel 223 and disposed rearwardly of the distal end thereof, such as to allow for a gas flow through the delivery channel 223 in the event that the distal end of the delivery channel 223 becomes obstructed.

Operation of the delivery device is the same as for the above-described third embodiment.

FIGS. 49 to 58 illustrate a nasal delivery device in accordance with an eighth embodiment of the present invention.

The delivery device comprises a housing 315, a nosepiece assembly 317 for fitting in a nasal cavity of a subject, and a mouthpiece unit 319 through which the subject exhales to actuate the delivery device.

The nosepiece assembly 317 comprises a nosepiece 320 which is attached to the housing 315 and defines a delivery channel 323 which is in fluid communication with the mouthpiece unit 319 such that an air flow is delivered into and through the nasal airway of the subject on exhalation by the subject through the mouthpiece unit 319, and an outlet unit 324 which is disposed within the nosepiece 320 for delivering substance into the nasal airway of the subject.

Figure 50:
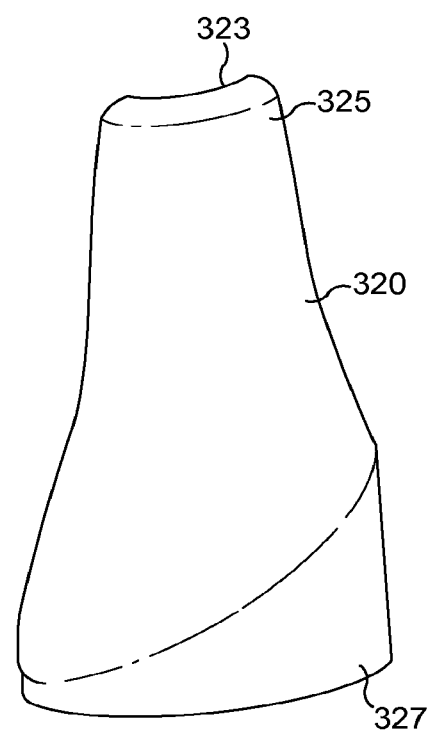
FIG. 50 illustrates a fragmentary perspective view of the nosepiece of the delivery device of FIG. 49 (other side symmetrical)
Figure 51:
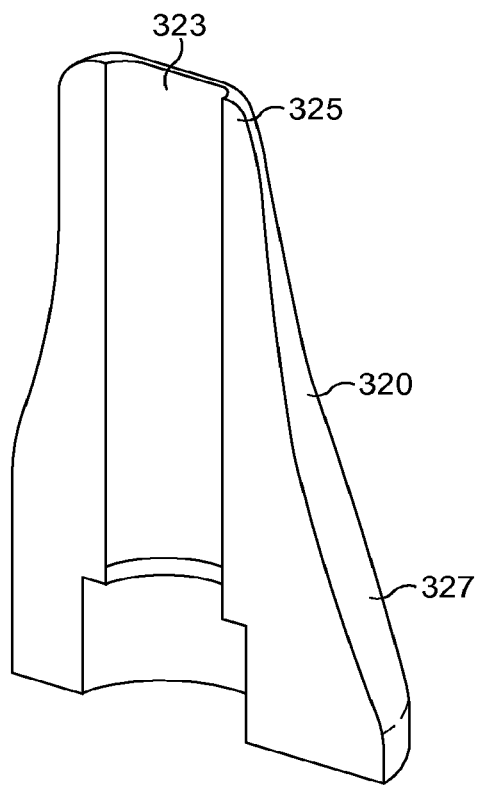
FIG. 51 illustrates a fragmentary, sectional perspective view of the nosepiece of the delivery device of FIG. 49 (other side symmetrical)
Figure 52:
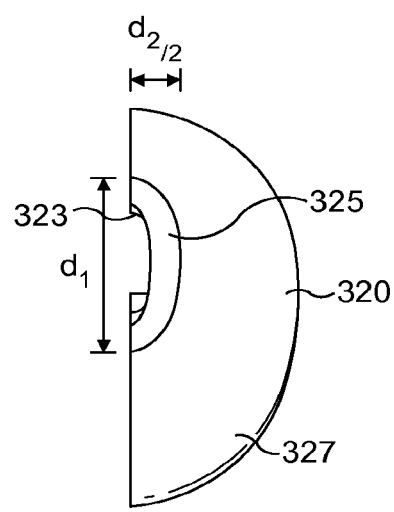
FIG. 52 illustrates a fragmentary plan view of the nosepiece of the delivery device of FIG. 49 (other side symmetrical)

In this embodiment, as particularly illustrated in FIGS. 50 to 52, the nosepiece 320 is generally frusto-conical in shape and includes a tip element 325 of asymmetric, elongate section, in having a dimension d1 in a first, sagittal direction which is substantially greater than a dimension d2 in a second, lateral direction which is orthogonal to the first, sagittal direction. In this embodiment the dimension d1 in the sagittal direction is at least twice that of the dimension d2 in the lateral direction. In one embodiment the dimension d2 in the lateral direction is not more than 6 mm and more preferably not more than 4 mm.

In this embodiment the tip element 325 extends substantially axially to the longitudinal axis of the nosepiece 320.

In this embodiment the nosepiece 320 further comprises a sealing element 326, in this embodiment a tapered, annular section, which acts both to provide a seal with the nares of the nostril of the nasal cavity of the subject and determine the extent of the insertion of the outlet unit 324 of the nosepiece assembly 317 into the nasal cavity of the subject. In a preferred embodiment the distal end of the outlet unit 324 is configured to extend at least about 2 cm, preferably at least about 3 cm, more preferably at least about 4 cm, and preferably from about 2 cm to about 4 cm, into the nasal cavity of the subject.

In this embodiment the nosepiece 320 is formed as a substantially rigid structure, here formed of a plastics material.

With this configuration, as will be described in more detail hereinbelow, on insertion of the nosepiece 320 into the nasal cavity of the subject, the longer, sagittal section of the tip element 325 of the nosepiece 320 becomes aligned in the sagittal plane and acts to engage upper and lower walls of the nasal cavity of the subject and cause the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 320 in the nasal cavity of the subject, with the lower wall of the nasal cavity of the subject, in being a relatively-hard structure, acting as a reference for the expansion.

This expansion further acts to tension the lateral walls of the nasal cavity of the subject which defines the nasal valve, which causes the lateral walls of the nasal cavity to be urged into sealing contact with the nosepiece 320.

In this embodiment the outlet unit 324 comprises a nozzle 345 for delivering substance to the nasal airway of the subject.

Figure 53:
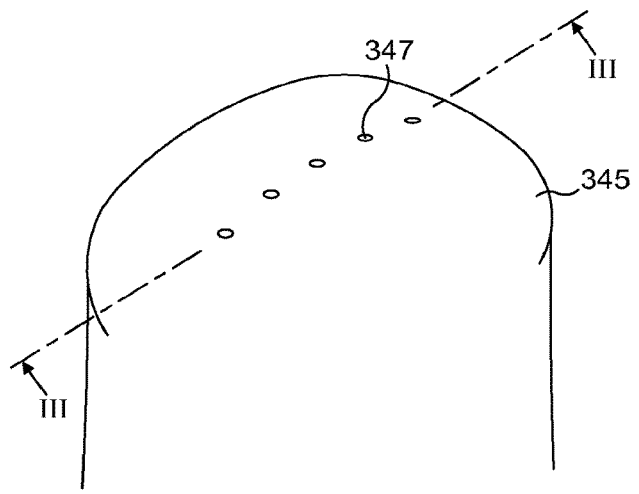
FIG. 53 illustrates a fragmentary perspective view of the nozzle of the outlet unit of the delivery device of FIG. 49.
Figure 54:
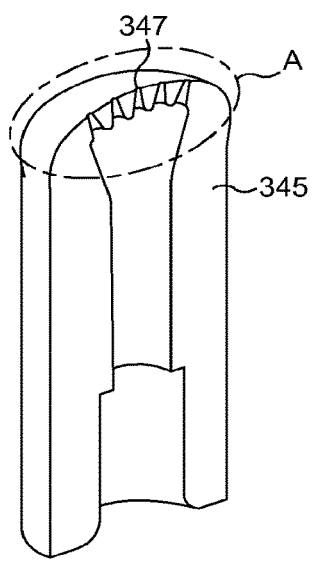
FIG. 54 illustrates a vertical sectional view (along section III-III in FIG. 53) of the nozzle of FIG. 53.
Figure 55:
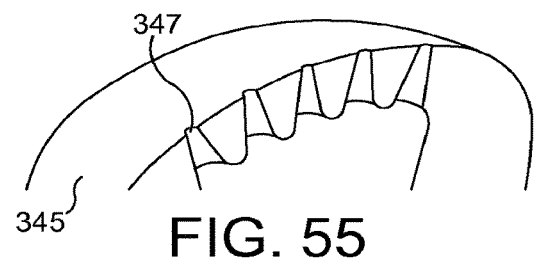
FIG. 55 illustrates an enlarged view of detail A in FIG. 54.

In this embodiment, as illustrated in FIGS. 53 to 55, the nozzle 345 includes a plurality of nozzle outlets 347 which provide a plurality of jets as columns of substance, either as a liquid or powder jet.

In this embodiment the nozzle 345 of the outlet unit 324 is configured to deliver an asymmetric profile, with the jet spray having a significantly greater spray angle in the vertical, sagittal plane $\alpha$ than in the horizontal plane $\beta$. Such jets have been found to be particularly advantageous in the delivery of substance to posterior regions of the nasal cavities, in particular the olfactory region.

In a preferred embodiment the jet spray angle in the vertical, sagittal plane $\alpha$ is greater than about 35°, more preferably greater than about 40°, still more preferably greater than about 45° and yet more preferably greater than about 50°.

In this embodiment the nozzle outlets are aligned in the vertical, sagittal direction and thus the jet angle in the horizontal plane $\beta$ approaches 0°. In other embodiments the jet angle in the horizontal plane $\beta$ is not more than about 35°, more preferably not more than about 30°, still more preferably not more than about 25°, yet more preferably not more than about 20°, still yet more preferably not more than about 15°, yet further more preferably not more than about 10° and still yet further more preferably not more than about 5°.

In this embodiment the jet spray presents a substantially rectangular spray zone.

The delivery device further comprises a substance supply unit 349 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 345 of the outlet unit 324 to deliver substance from the nosepiece assembly 317, in this embodiment as a plurality of liquid jets.

In this embodiment the substance supply unit 349 is a multi-dose unit for delivering a plurality of metered doses of substance. In another embodiment the substance supply unit 349 could be a single-dose unit for delivering a single metered dose of substance.

The substance supply unit 349 is pre-primeable, in this embodiment by loading a resilient element, and includes a breath-actuated release mechanism 351 which, when triggered, releases the resilient element and actuates the substance supply unit 349 to deliver a metered dose of substance through the nozzle 345 of the outlet unit 324.

In this embodiment the release mechanism 351 is configured to cause actuation of the substance supply unit 349 on generation of a predetermined flow rate through the delivery channel 323 of the nosepiece 320.

In another embodiment the release mechanism 351 could be configured to cause actuation of the substance supply unit 349 on generation of a predetermined pressure within the delivery channel 323 of the nosepiece 320.

In a further embodiment the release mechanism 351 could be configured to cause actuation of the substance supply unit 349 on generation of either one of a predetermined flow rate through the delivery channel 323 of the nosepiece 320 or a predetermined pressure within the delivery channel 323 of the nosepiece 320.

In an alternative embodiment the substance supply unit 349 could comprise a mechanical delivery pump, in particular a liquid delivery pump or a powder delivery pump, which delivers metered doses of a substance on actuation thereof.

In another alternative embodiment the substance supply unit 239 could comprise a dry powder delivery unit which delivers metered doses of a substance, as a dry powder, on actuation thereof.

In yet another alternative embodiment the substance supply unit 349 could comprise a nebulizer which delivers metered doses of a substance, as an aerosol spray, on actuation thereof.

Operation of the delivery device will now be described hereinbelow with reference to FIGS. 56 to 58 of the accompanying drawings.

Figure 56:
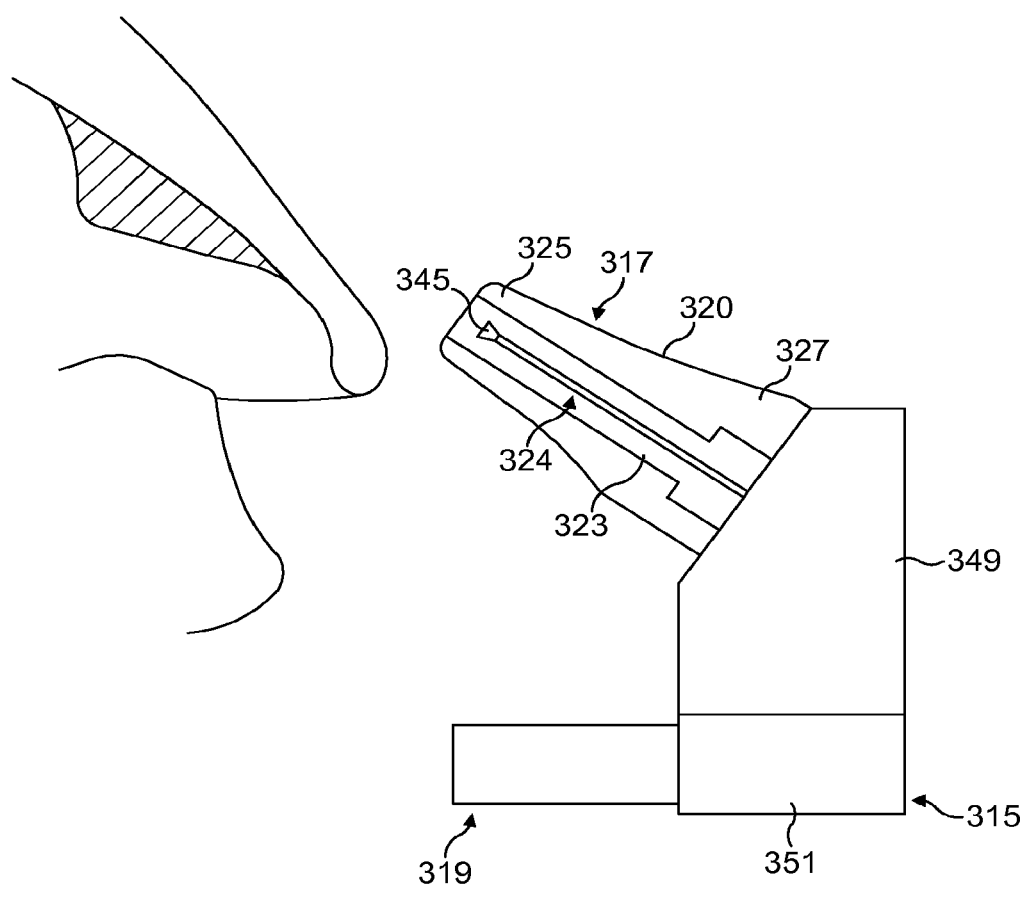
FIG. 56 illustrates the delivery device of FIG. 49 prior to insertion into a nasal cavity of a subject.
Figure 57:
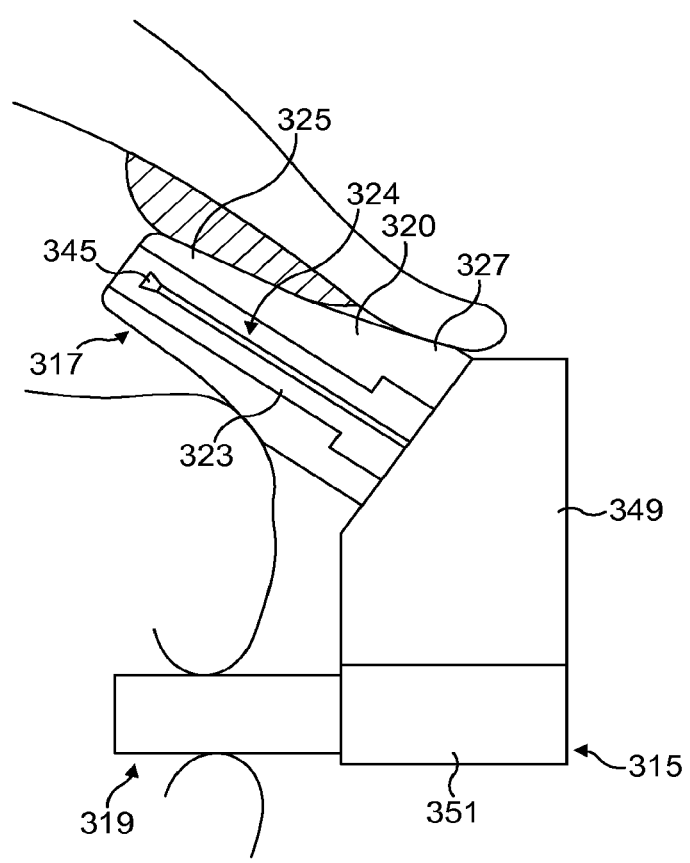
FIG. 57 illustrates the delivery device of FIG. 49 inserted into a nasal cavity of the subject prior to operation.

Referring to FIGS. 56 and 57, the nosepiece assembly 317 is first inserted into one of the nasal cavities of a subject until the sealing member 327 abuts the nares of the nostril of the subject, at which point the distal end of the outlet unit 324 typically extends from about 2 cm to about 4 cm into the nasal cavity of the subject, and the mouthpiece unit 319 is then gripped in the lips of the subject.

As illustrated, insertion of the nosepiece 320 into the nasal cavity of the subject acts to cause the longer, sagittal section of the tip element 325 of the nosepiece 320 to become aligned in the sagittal plane and engage upper and lower walls of the nasal cavity of the subject, which engagement causes the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 320 in the nasal cavity of the subject, with the lower wall of the nasal cavity of the subject, in being a relatively-hard structure, acting as a reference for the expansion. This expansion further acts to tension the lateral walls of the nasal cavity of the subject which defines the nasal valve, which causes the lateral walls of the nasal cavity to be urged into sealing contact with the nosepiece 320.

Figure 58:
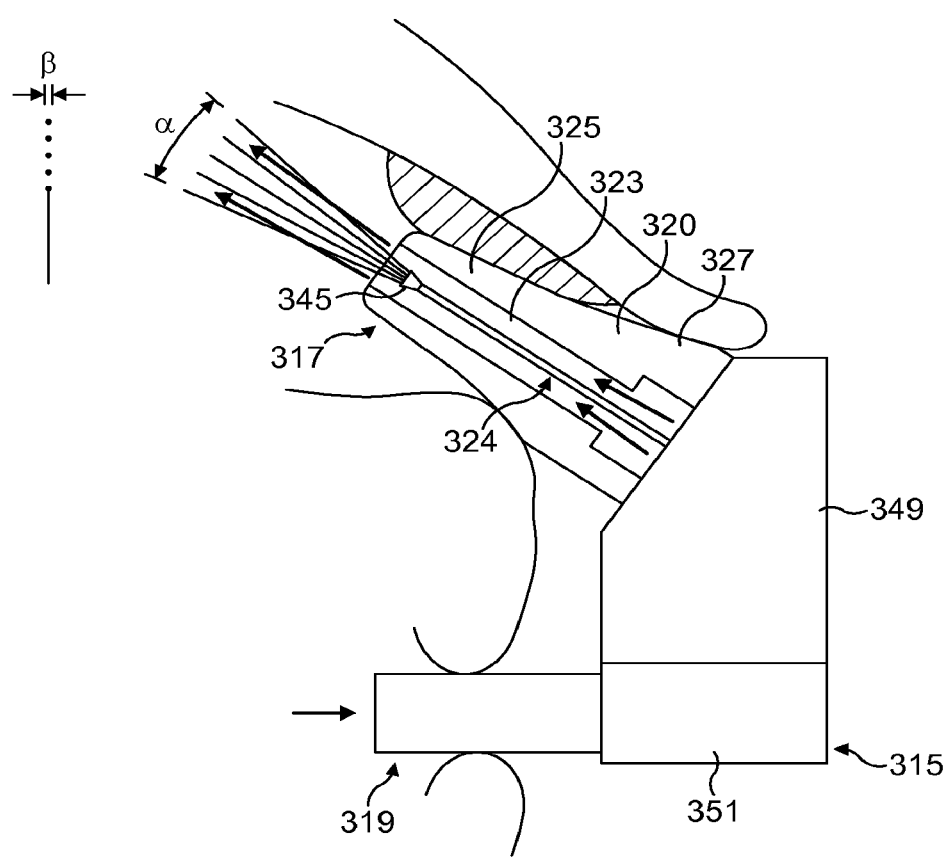
FIG. 58 illustrates the delivery device of FIG. 49 following actuation of the substance supply unit.
Figure 59:
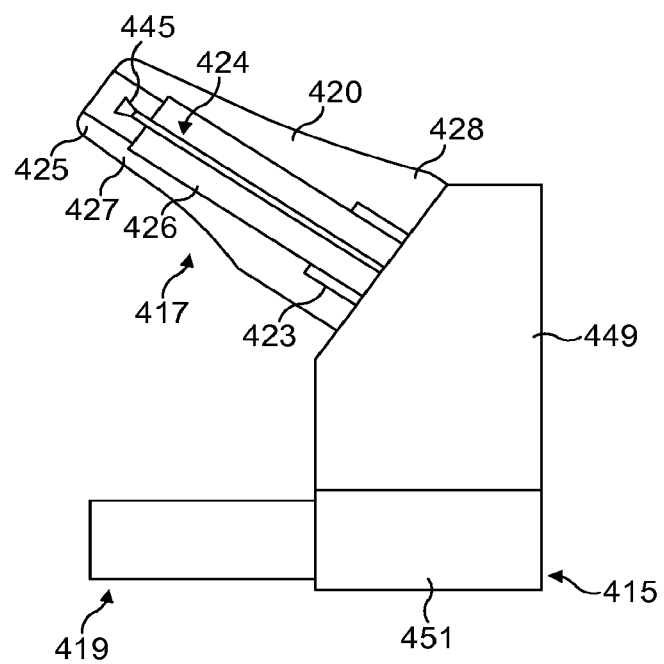
FIG. 59 illustrates a nasal delivery device in accordance with a ninth embodiment of the present invention.

Referring to FIG. 58, the subject then begins to exhale through the mouthpiece unit 319, which exhalation acts to close the oropharyngeal velum of the subject and drive an air flow through the delivery channel 323 of the nosepiece 320, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 323 of the nosepiece 320 reaches a predetermined value, the release mechanism 351 is triggered to actuate the substance supply unit 349 to deliver a metered dose of a substance to the nozzle 345 of the outlet unit 324 and into the nasal cavity of the subject, in this embodiment as an asymmetric jet spray comprising a plurality of liquid jets. In an alternative embodiment the release mechanism 351 could be triggered on the generation of a predetermined pressure in the delivery channel 323 of the nosepiece 320.

Following exhalation, the subject then releases the mouthpiece unit 319 and the nosepiece assembly 317 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 349.

FIGS. 59 to 67 illustrate a nasal delivery device in accordance with a ninth embodiment of the present invention.

The delivery device comprises a housing 415, a nosepiece assembly 417 for fitting in a nasal cavity of a subject, and a mouthpiece unit 419 through which the subject exhales to actuate the delivery device.

The nosepiece assembly 417 comprises a nosepiece 420 which is attached to the housing 415 and defines a delivery channel 423 which is in fluid communication with the mouthpiece unit 419 such that an air flow is delivered into and through the nasal airway of the subject on exhalation by the subject through the mouthpiece unit 419, and an outlet unit 424 which is disposed within the nosepiece 420 for delivering substance into the nasal airway of the subject.

Figure 60:
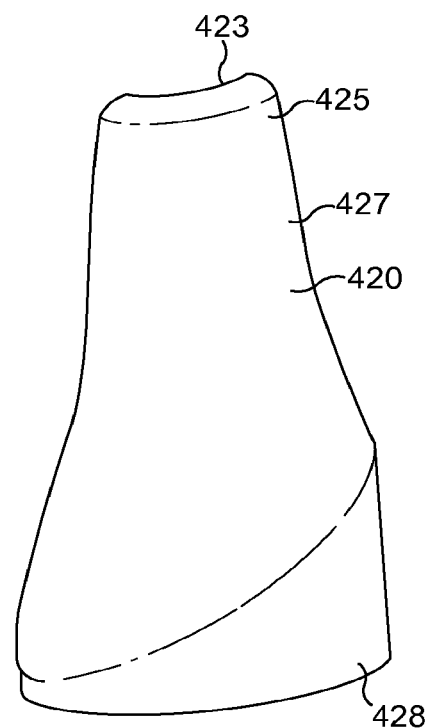
FIG. 60 illustrates a fragmentary perspective view of the nosepiece of the delivery device of FIG. 59 (other side symmetrical)
Figure 61:
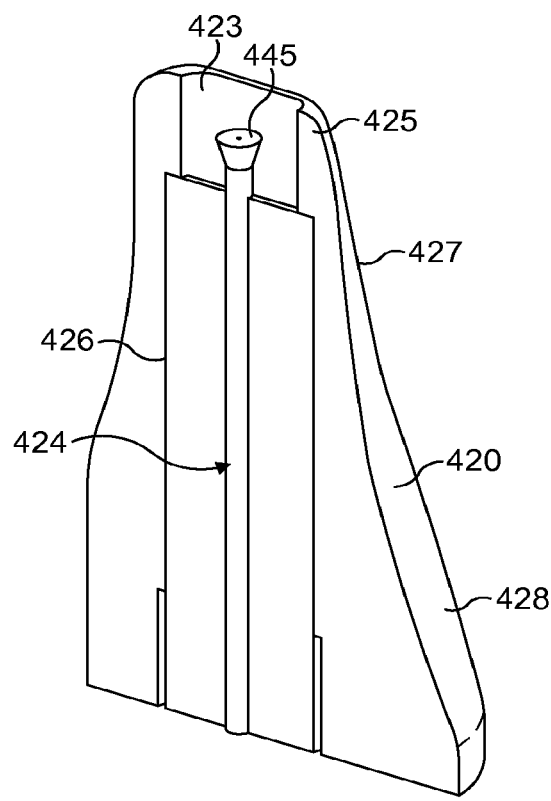
FIG. 61 illustrates a fragmentary, sectional perspective view of the nosepiece of the delivery device of FIG. 59 (other side symmetrical)
Figure 62:
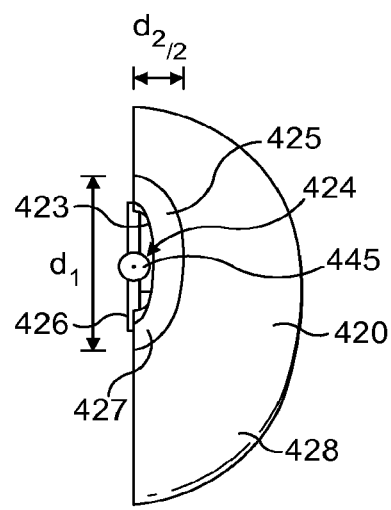
FIG. 62 illustrates a fragmentary plan view of the nosepiece of the delivery device of FIG. 59 (other side symmetrical)

In this embodiment, as particularly illustrated in FIGS. 60 to 62, the nosepiece 420 comprises a nosepiece member 425 which acts to engage the nasal cavity of the subject and a support member 426 which acts structurally to support the nosepiece member 425, such as to confer a required rigidity in the sagittal plane, as will be described in more detail hereinbelow.

In this embodiment the nosepiece member 425 is generally frusto-conical in shape and includes a tip element 427 of asymmetric, elongate section, in having a dimension d1 in a first, sagittal direction which is substantially greater than a dimension d2 in a second, lateral direction which is orthogonal to the first, sagittal direction. In this embodiment the dimension d1 in the sagittal direction is at least twice that of the dimension d2 in the lateral direction. In one embodiment the dimension d2 in the lateral direction is not more than 6 mm and more preferably not more than 4 mm.

In this embodiment the tip element 427 extends substantially axially to the longitudinal axis of the nosepiece 420.

In this embodiment the nosepiece member 425 further includes a sealing element 428, in this embodiment a tapered, annular section, which acts both to provide a seal with the nares of the nostril of the nasal cavity of the subject and determine the extent of the insertion of the outlet unit 424 of the nosepiece assembly 417 into the nasal cavity of the subject. In a preferred embodiment the distal end of the outlet unit 424 is configured to extend at least about 2 cm, preferably at least about 3 cm, more preferably at least about 4 cm, and preferably from about 2 cm to about 4 cm, into the nasal cavity of the subject. In a preferred embodiment the distal end of the outlet unit 424 extends into the bony part of the nasal valve, or at least as far into the nasal cavity as possible with the outlet unit 424 aligned with the nasal slit, such that the outlet unit 424 targets substance at the upper posterior region of the nasal cavity, and in particular the olfactory region.

In this embodiment the nosepiece member 425 is formed as a flexible or semi-rigid structure, here formed of a plastics material, which allows the nosepiece 420 to conform to the nasal cavity of the subject, where the nasal cavities of different subjects can differ quite markedly.

In this embodiment the support member 426 confers rigidity to the nosepiece member 425 in both the axial direction, such as to prevent the collapse of the nosepiece 420 on insertion into the nasal cavity, and the vertical, sagittal plane along the elongate, sagittal direction of the tip element 427 of the nosepiece member 425, such as to enable expansion of the nasal cavity in the vertical, sagittal plane, as will be described in more detail hereinbelow.

Figure 63:
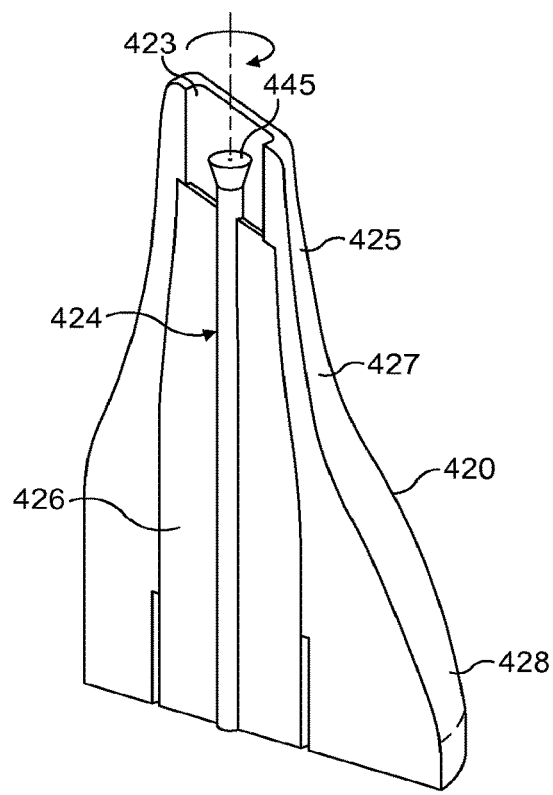
FIG. 63 illustrates a fragmentary, sectional perspective view of the nosepiece of the delivery device of FIG. 59 where twisted about the longitudinal axis of the nosepiece.
Figure 64:
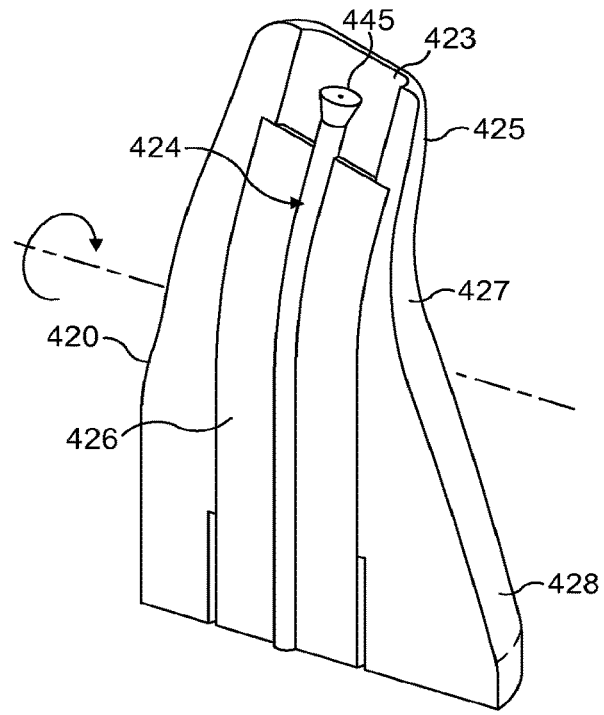
FIG. 64 illustrates a fragmentary, sectional perspective view of the nosepiece of the delivery device of FIG. 59 where bent about an axis orthogonal to the longitudinal axis of the nosepiece and extending in the plane of the support member of the nosepiece.

In this embodiment the support member 426 comprises an elongate plate, here a plastics plate, which extends along a length of the nosepiece member 425 in the elongate, sagittal direction of the tip element 427 of the nosepiece member 425. This plate is flexible in allowing for torsional flexing, as illustrated in FIG. 63, and flexing over the major surface thereof, as illustrated in FIG. 64, but presents a substantially rigid structure in the plane of the plate, such as not to allow for flexing in the plane of the plate.

In an alternative embodiment the support member 426 could take the form of a living hinge, which comprises a plurality of rigid elements interconnected by flexible elements, which allow for torsional and bending moments.

In this embodiment the outlet unit 424 comprises a nozzle 445 for delivering substance to the nasal airway of the subject.

In this embodiment the nozzle 445 is attached to the support member 426, and can be integrally formed therewith in one embodiment.

In this embodiment the nozzle 445 is configured to provide an aerosol spray, either as a liquid or powder aerosol.

In an alternative embodiment the nozzle 445 could be configured to deliver a jet as a column of substance, either as a liquid or powder jet.

With this configuration, as will be described in more detail hereinbelow, on insertion of the nosepiece 420 into the nasal cavity of the subject, the flexibility of the nosepiece 420 facilitates the longer, sagittal section of the tip element 427 of the nosepiece member 425 in becoming aligned in the sagittal plane and acts to engage upper and lower walls of the nasal cavity of the subject and, by virtue of the rigidity of the nosepiece 420 in the sagittal plane, cause the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 420 in the nasal cavity of the subject, with the lower wall of the nasal cavity of the subject, in being a relatively-hard structure, acting as a reference for the expansion.

This expansion further acts to tension the lateral walls of the nasal cavity of the subject which defines the nasal valve, which causes the lateral walls of the nasal cavity to be urged into sealing contact with the nosepiece 420.

In this embodiment the nozzle 445 of the outlet unit 424 is configured to deliver an asymmetric aerosol spray, with the aerosol spray having a significantly greater spray angle in the vertical, sagittal plane α than in the horizontal plane β. Such an aerosol spray has been found to be particularly advantageous in the delivery of substance to posterior regions of the nasal cavities, in particular the olfactory region.

In a preferred embodiment the spray angle in the vertical, sagittal plane α is greater than about 35°, more preferably greater than about 40°, still more preferably greater than about 45° and yet more preferably greater than about 50°.

In a preferred embodiment the spray angle in the horizontal plane β is not more than about 35°, more preferably not more than about 30°, still more preferably not more than about 25°, yet more preferably not more than about 20°, and still yet more preferably not more than about 15°.

In this embodiment the aerosol spray presents an elliptical spray zone.

In another embodiment the aerosol spray could present a substantially rectangular spray zone.

The delivery device further comprises a substance supply unit 449 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 445 of the outlet unit 424 to deliver substance from the nosepiece assembly 417, in this embodiment as an aerosol spray.

In this embodiment the substance supply unit 449 is a multi-dose unit for delivering a plurality of metered doses of substance. In another embodiment the substance supply unit 449 could be a single-dose unit for delivering a single metered dose of substance.

The substance supply unit 449 is pre-primeable, in this embodiment by loading a resilient element, and includes a breath-actuated release mechanism 451 which, when triggered, releases the resilient element and actuates the substance supply unit 449 to deliver a metered dose of substance through the nozzle 445 of the outlet unit 424.

In this embodiment the release mechanism 451 is configured to cause actuation of the substance supply unit 449 on generation of a predetermined flow rate through the delivery channel 423 of the nosepiece 420.

In another embodiment the release mechanism 451 could be configured to cause actuation of the substance supply unit 449 on generation of a predetermined pressure within the delivery channel 423 of the nosepiece 420.

In a further embodiment the release mechanism 451 could be configured to cause actuation of the substance supply unit 449 on generation of either one of a predetermined flow rate through the delivery channel 423 of the nosepiece 420 or a predetermined pressure within the delivery channel 423 of the nosepiece 420.

In an alternative embodiment the substance supply unit 449 could comprise a mechanical delivery pump, in particular a liquid delivery pump or a powder delivery pump, which delivers metered doses of a substance on actuation thereof.

In another alternative embodiment the substance supply unit 449 could comprise a dry powder delivery unit which delivers metered doses of a substance, as a dry powder, on actuation thereof.

In yet another alternative embodiment the substance supply unit 449 could comprise a nebulizer which delivers metered doses of a substance, as an aerosol spray, on actuation thereof.

Operation of the delivery device will now be described hereinbelow with reference to FIGS. 65 to 67 of the accompanying drawings.

Figure 65:
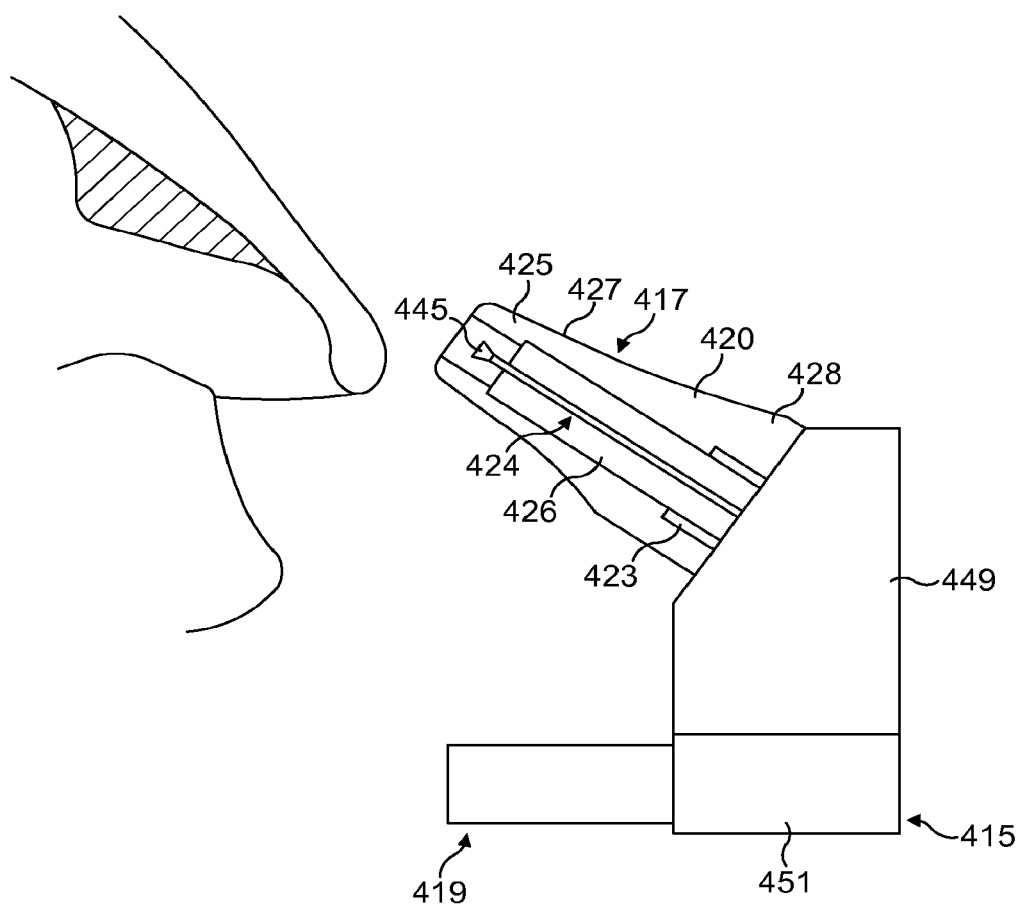
FIG. 65 illustrates the delivery device of FIG. 59 prior to insertion into a nasal cavity of a subject.
Figure 66:
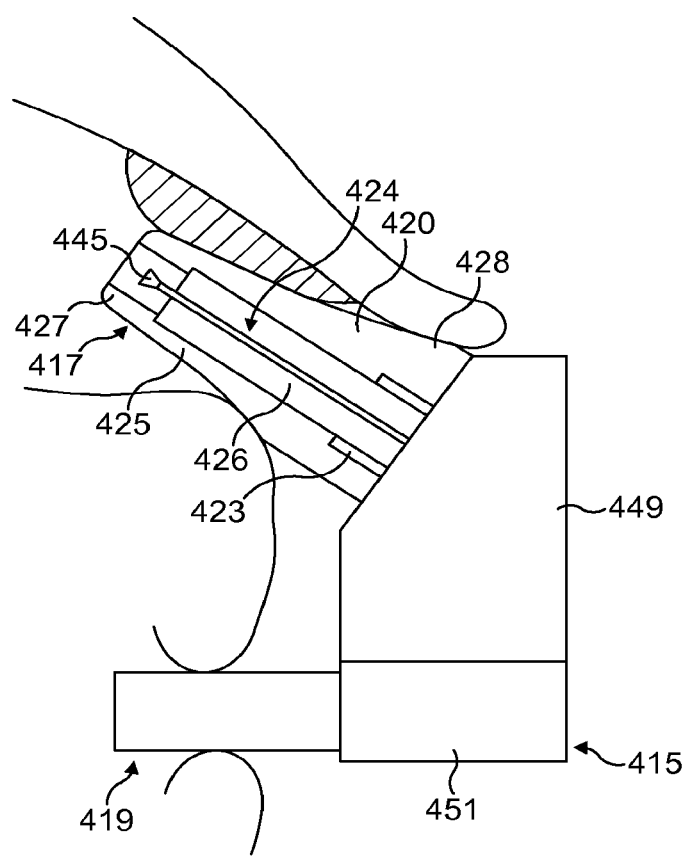
FIG. 66 illustrates the delivery device of FIG. 59 inserted into a nasal cavity of the subject prior to operation.

Referring to FIGS. 65 and 66, the nosepiece assembly 417 is first inserted into one of the nasal cavities of a subject until the sealing element 428 of the nosepiece member 425 abuts the nares of the nostril of the subject, at which point the distal end of the outlet unit 424 typically extends from about 2 cm to about 4 cm into the nasal cavity of the subject, and the mouthpiece unit 419 is then gripped in the lips of the subject.

As illustrated, insertion of the nosepiece 420 into the nasal cavity of the subject acts to cause the longer, sagittal section of the tip element 427 of the nosepiece member 425 to become aligned in the sagittal plane and engage upper and lower walls of the nasal cavity of the subject, which engagement causes the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 420 in the nasal cavity of the subject, with the lower wall of the nasal cavity of the subject, in being a relatively-hard structure, acting as a reference for the expansion. This expansion further acts to tension the lateral walls of the nasal cavity of the subject which defines the nasal valve, which causes the lateral walls of the nasal cavity to be urged into sealing contact with the nosepiece 420.

Figure 67:
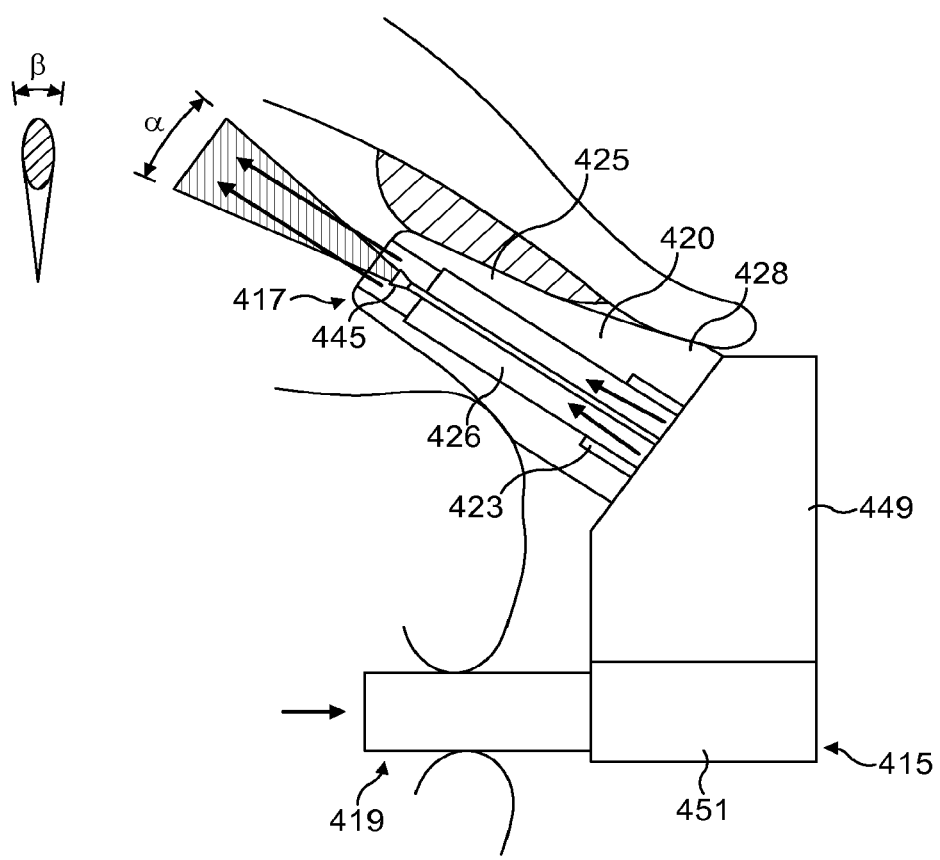
FIG. 67 illustrates the delivery device of FIG. 59 following actuation of the substance supply unit.

Referring to FIG. 67, the subject then begins to exhale through the mouthpiece unit 419, which exhalation acts to close the oropharyngeal velum of the subject and drive an air flow through the delivery channel 423 of the nosepiece 420, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 423 of the nosepiece 420 reaches a predetermined value, the release mechanism 451 is triggered to actuate the substance supply unit 449 to deliver a metered dose of a substance to the nozzle 445 of the outlet unit 424 and into the nasal cavity of the subject, in this embodiment as an asymmetric aerosol spray. In an alternative embodiment the release mechanism 451 could be triggered on the generation of a predetermined pressure in the delivery channel 423 of the nosepiece 420.

Following exhalation, the subject then releases the mouthpiece unit 419 and the nosepiece assembly 417 is withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 449.

Finally, it will be understood that the present invention has been described in its preferred embodiments and can be modified in many different ways without departing from the scope of invention as defined by the appended claims.

For example, in one modification, the nosepieces of the above-described third to eighth embodiments could be other than elliptical in section, such as an elongate, triangular section, with the base of the triangle defining a lower edge of the nosepiece.

In another modification the outlet units of the above-described embodiments could be configured such that the nozzles thereof are extendable in a forward direction following insertion of the nosepieces, for example, in the manner of a telescopic element, such as to extend further posterior into the nasal cavity.

In a further modification of the delivery device of the seventh-described embodiment, the flexible coupling 259 can be integrated with the support member 226 of the nosepiece 220.

Figure 68:
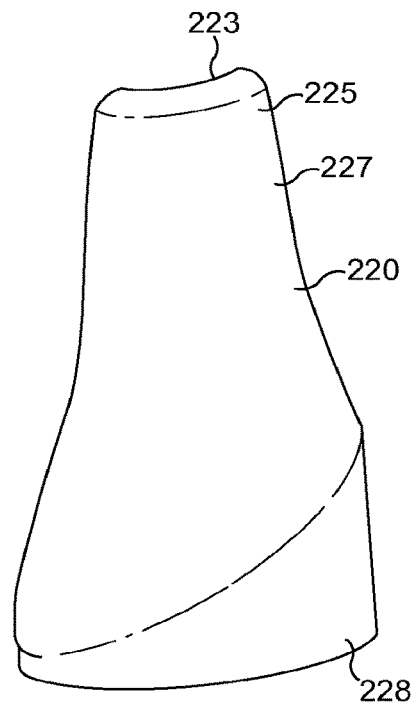
FIG. 68 illustrates a fragmentary perspective view of a nosepiece as one modification of the nosepiece of the delivery device of FIG. 42 (other side symmetrical)
Figure 69:
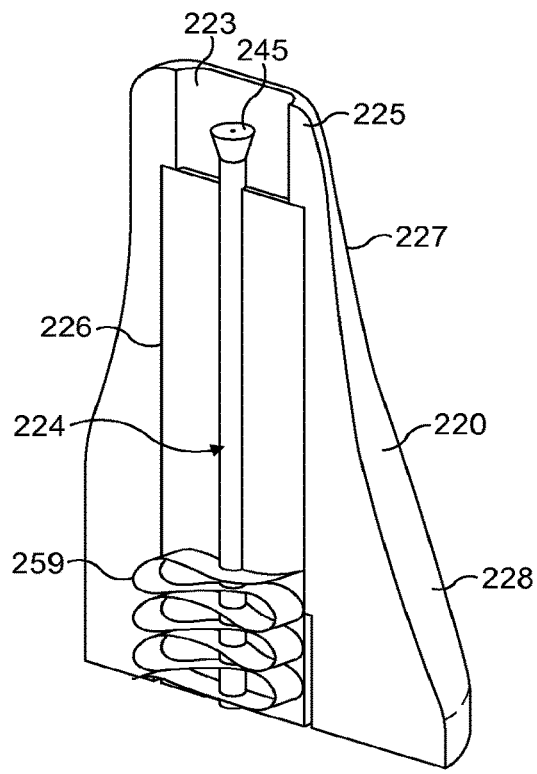
FIG. 69 illustrates a fragmentary, sectional perspective view of the nosepiece of FIG. 68 (other side symmetrical)
Figure 70:
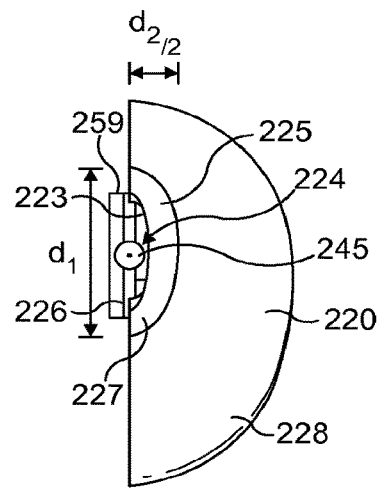
FIG. 70 illustrates a fragmentary plan view of the nosepiece of FIG. 68 (other side symmetrical).

FIGS. 68 to 70 illustrate one such embodiment. In this embodiment the flexible coupling 259, the support member 226 and the outlet unit 224 are formed as a single, integral unit, typically of a plastics material. In this embodiment the flexible coupling 259 allows for limited axial compression of the nosepiece 220 by compression of the flexible coupling 259 and also allows for limited bending of the support member 226 about the flexible coupling 259, which assist in insertion of the nosepiece 220 into the nasal cavity. In this embodiment the upper part of the support member 226 is still substantially rigid in the plane thereof, such as to provide for vertical, sagittal expansion of the nasal cavity, in particular the collapsed region at the upper, lateral wall of the nasal cavity.

In an alternative embodiment the flexible coupling 259 could have a simpler geometric shape, in one example as a section of the support member 226 of reduced thickness, which confers the limited compressibility and flexibility to the flexible coupling 259, but yet which confers the required rigidity to the support member 226, in particular the upper part thereof, as to achieve the vertical, sagittal expansion of the nasal cavity.

REFERENCES

1. Cole, P, The Respiratory Role of the Upper Airways, a selective clinical and pathophysiological review. 1993, Mosby-Year Book Inc. ISBN1.55664-390-X.
2. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, S.C., USA, 1934.
3. Zacharek, M A et al, Sagittal and Coronal Dimensions of the Ethmoid Roof: A Radioanatomic Study, Am J Rhinol 2005, Vol 19, pages 348 to 352.

The invention claimed is:

1. A method of treating migraine in a subject by delivering an anti-migraine composition to a nasal cavity of the subject, comprising:
    fitting a nosepiece to one nostril of the subject through which the anti-migraine composition is delivered to the nasal cavity, wherein a lateral cross section of at least a tip portion of the nosepiece has a longer dimension in a first direction than a second direction orthogonal to the first direction, such that the longer dimension of the tip portion of the nosepiece is substantially aligned with the direction of the sagittal plane of the subject and engages lower and upper surfaces of the nasal cavity and expands the nasal cavity in the sagittal plane;
    the subject exhaling through a mouthpiece to close an oropharyngeal velum of the subject; and
    delivering the anti-migraine composition through the nosepiece and into the nasal cavity of the subject.

2. The method of claim 1, wherein the lateral section of the tip portion of the nosepiece is substantially elliptical.

3. The method of claim 1, wherein the lateral cross section of the tip portion of the nosepiece is substantially rectangular.

4. The method of claim 1, wherein the tip portion of the nosepiece is inclined in the sagittal plane relative to a longitudinal axis of the nosepiece.

5. The method of claim 1, wherein the nosepiece extends into the nasal valve of the subject, such that the longer dimension of the tip portion of the nosepiece engages lower and upper surfaces of the nasal cavity of the subject at the nasal valve and expands the nasal valve of the subject in the sagittal plane.

6. The method of claim 1, wherein the anti-migraine composition comprises a powder.

7. The method of claim 1, wherein the nosepiece and the mouthpiece are fluidly connected, whereby an exhalation air flow generated by an exhalation breath of the subject is delivered from the nosepiece into the nasal cavity of the subject.

8. The method of claim 7, wherein the exhalation air flow entrains the anti-migraine composition.

9. The method of claim 1, wherein the anti-migraine composition is delivered to an upper posterior region of the nasal cavity which is above the inferior meatus.

10. The method of claim 9, wherein the upper posterior region includes the olfactory region.

11. A method of treating nasal polyps in a subject by delivering a topical nasal steroid to a nasal cavity of the subject, comprising:
    fitting a nosepiece to one nostril of the subject through which the nasal steroid is delivered to the nasal cavity, wherein a lateral cross section of at least a tip portion of the nosepiece has a longer dimension in a first direction than a second direction orthogonal to the first direction, such that the longer dimension of the tip portion of the nosepiece is substantially aligned with the direction of the sagittal plane of the subject and engages lower and upper surfaces of the nasal cavity and expands the nasal cavity in the sagittal plane;
    the subject exhaling through a mouthpiece to close an oropharyngeal velum of the subject; and
    delivering the nasal steroid through the nosepiece and into the nasal cavity of the subject.

12. The method of claim 11, wherein the lateral section of the tip portion of the nosepiece is substantially elliptical.

13. The method of claim 11, wherein the lateral cross section of the tip portion of the nosepiece is substantially rectangular.

14. The method of claim 11, wherein the tip portion of the nosepiece is inclined in the sagittal plane relative to a longitudinal axis of the nosepiece.

15. The method of claim 11, wherein the nosepiece extends into the nasal valve of the subject, such that the longer dimension of the tip portion of the nosepiece engages lower and upper surfaces of the nasal cavity of the subject at the nasal valve and expands the nasal valve of the subject in the sagittal plane.

16. The method of claim 11, wherein the nasal steroid comprises a liquid.

17. The method of claim 11, wherein the nasal steroid is delivered as a liquid aerosol.

18. The method of claim 11, wherein the liquid aerosol is a liquid spray.

19. The method of claim 18, wherein a spray angle of the liquid spray in the sagittal direction is greater than 35°.

20. The method of claim 18, wherein a spray angle of the liquid spray in the sagittal direction is greater than 40°.

21. The method of claim 18, wherein a spray angle of the liquid spray in the sagittal direction is greater than 45°.

22. The method of claim 11, wherein the nosepiece and the mouthpiece are fluidly connected, whereby an exhalation air flow generated by an exhalation breath of the subject is delivered from the nosepiece into the nasal cavity of the subject.

23. The method of claim 11, wherein the nasal steroid is delivered to an upper posterior region of the nasal cavity which is above the inferior meatus.

24. The method of claim 23, wherein the upper posterior region includes the middle meatus.

25. A nasal delivery device for delivering substance to a nasal cavity of a subject, the delivery device comprising:
- a nosepiece unit including:
    - a nosepiece for fitting to a nostril of a subject, the nosepiece having a tip element; and
    - a nozzle through which substance is delivered to a nasal cavity of the subject;
    - wherein a lateral cross section of the tip element has a longer dimension in a first direction than a second direction orthogonal to the first direction, such that, when the nosepiece is inserted in the nasal cavity of the subject, the longer dimension of the tip element is substantially aligned with the direction of the sagittal plane of the subject and acts to engage lower and upper surfaces of the nasal cavity and expand the same in the sagittal plane; and
- a delivery unit for delivering substance through the nozzle of the nosepiece.

* * * * *

UNITED STATES PATENT AND TRADEMARK OFFICE
CERTIFICATE OF CORRECTION

PATENT NO. : 10,124,132 B2
APPLICATION NO. : 15/051622
DATED : November 13, 2018
INVENTOR(S) : Per Gisle Djupesland Page 1 of 1

It is certified that error appears in the above-identified patent and that said Letters Patent is hereby corrected as shown below:

On the Title Page

(60) "Division of application No. 14/047,390, filed on Oct. 7, 2013, which is a continuation of application No." should read --Continuation of application No. 14/047,390, filed on Oct. 7, 2013, which is a continuation of application No.--.

Signed and Sealed this
Eighth Day of January, 2019

Andrei Iancu
*Director of the United States Patent and Trademark Office*